United States Patent [19]

Engel et al.

[11] Patent Number: 4,931,436
[45] Date of Patent: Jun. 5, 1990

[54] CONDENSED DIAZEPINONES, PROCESSES FOR PREPARING THEM AND PHARMACEUTICAL COMPOSITIONS CONTAINING THESE COMPOUNDS

[75] Inventors: Wolfhard Engel, Biberach; Gunter Trummlitz, Warthausen; Wolfgang Eberlein, Biberach; Gerhard Mihm, Biberach; Norbert Mayer, Biberach, all of Fed. Rep. of Germany; Adriaan De Jonge, Driebergen, Netherlands; Klaus Rudolf, Biberach, Fed. Rep. of Germany

[73] Assignee: Dr. Karl Thomae GmbH, Biberach an der Riss, Fed. Rep. of Germany

[21] Appl. No.: 230,406

[22] Filed: Aug. 9, 1988

[51] Int. Cl.$^5$ .................. A61K 31/55; C07D 401/06; C07D 405/14
[52] U.S. Cl. ..................................... 514/220; 540/495
[58] Field of Search ..................... 540/495; 514/220

[56] References Cited

U.S. PATENT DOCUMENTS 4,550,107 10/1985 Engel et al. .................... 540/495

FOREIGN PATENT DOCUMENTS 0139627 10/1984 European Pat. Off. .......... 540/495

Primary Examiner—Robert T. Bond
Attorney, Agent, or Firm—David E. Frankhouser; Alan R. Stempel; Mary-Ellen M. Timbers

[57] ABSTRACT

New condensed diazepinones of general formula I are described

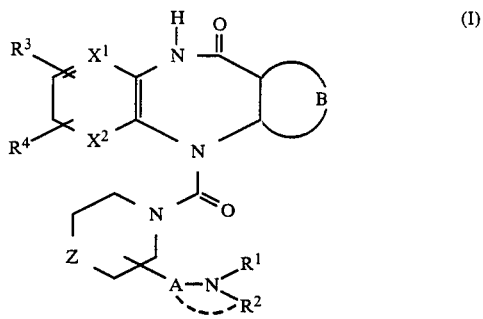

wherein B represents one of the divalent groups

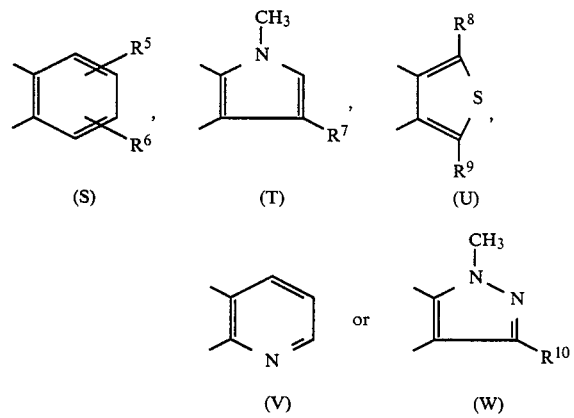

and $X^1$, $X^2$, A, $R^1$ to $R^{10}$ and Z are defined as in the specification.

6 Claims, No Drawings

CONDENSED DIAZEPINONES, PROCESSES FOR PREPARING THEM AND PHARMACEUTICAL COMPOSITIONS CONTAINING THESE COMPOUNDS

The invention relates to new condensed diazepinones, processes for preparing them and pharmaceutical compositions containing these compounds.

Condensed diazepinones with anti-ulcerative properties and an inhibitory effect on gastric juice secretion are already known from EP-A-Nos. 0 039 519 and 0 057 428 and from U.S. Pat. Nos. 3,660,380; 3,691,159; 4,213,984; 4,213,985; 4,210,648, 4,410,527; 4,424,225; 4,424,222 and 4,424,226.

EP-A-No. 0 156 191 describes how completely different, valuable pharmacological properties compared with the compounds of the above-mentioned publications can be induced by introducing new aminoacyl groups. The condensed diazepinones according to the invention are distinguished from these compounds by a substantially more powerful effect and marked resistance to hydrolysis, whilst having a comparable or better selectivity and resorption after oral administration.

The new condensed diazepinones have the general formula I,

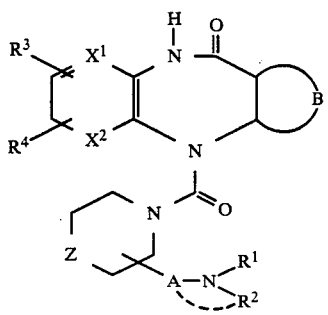

wherein B represents one of the divalent groups

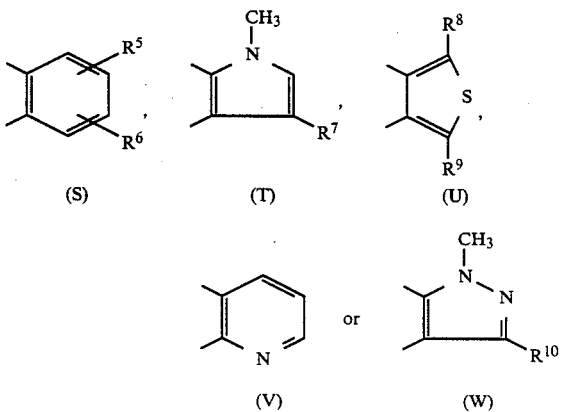

and $X^1$, $X^2$, A, $R^1$ to $R^{10}$ and Z are defined as follows:

$X^1$ and $X^2$ represent a =CH— group or, if B represents the above-mentioned divalent groups (S), (U) or (W), both $X^1$ and $X^2$ or only $X^1$ or only $X^2$ may represent a nitrogen atom;

A is a straight-chained or branched saturated alkylene group with two to seven carbon atoms which may also be interrupted by an oxygen or sulphur atom or by a methylimino or ethylimino group;

Z represents a single bond, an oxygen or sulphur atom or a methylene or 1,2-ethylene group;

$R^1$ represents a branched or unbranched alkyl group with 1 to 4 carbon atoms or a benzyl group;

$R^2$ represents a branched or unbranched alkyl group with 1 to 7 carbon atoms which may optionally also be substituted by a hydroxy group at its 2nd to 7th carbon atom, a cycloalkyl or cycloalkylmethyl group with 3 to 7 carbon atoms in the ring, wherein the cycloalkyl ring may optionally also be substituted by a hydroxy group;

$R^1$ and $R^2$ may, however, also form, together with the intermediate nitrogen atom, a 4- to 7-membered saturated, monocyclic, heterocyclic ring which may optionally be interrupted by an oxygen atom or by an N-CH$_3$ group;

$R^2$ may, however, also be linked to A via an alkylene bridge so that, in conjunction with the group $NR^1$, a saturated 5-, 6- or 7-membered heterocyclic ring system is produced;

$R^3$ is an alkyl group with 1 to 4 carbon atoms, a chlorine atom or a hydrogen atom;

$R^4$ is a hydrogen atom or a methyl group;

$R^5$ and $R^6$ each represent a hydrogen atom, a fluorine, chlorine or bromine atom or an alkyl group with 1 to 4 carbon atoms;

$R^7$ represents a hydrogen or chlorine atom or a methyl group;

$R^8$ represents a hydrogen atom or an alkyl group with 1 to 4 carbon atoms;

$R^9$ represents a hydrogen or halogen atom or an alkyl group with 1 to 4 carbon atoms and $R^{10}$ represents a hydrogen atom or a methyl group.

If B is the divalent group (T) and $R^7$ is a hydrogen atom, $R^3$ cannot be a chlorine atom and Z cannot be a sulphur atom.

Preferred compounds of general formula I above are those wherein either $X^1$ is a =CH— group, $X^2$ represents a nitrogen atom and B represents a divalent group (S), with the proviso that $R^3$, $R^4$ and $R^5$ are hydrogen atoms and $R^6$ is a hydrogen atom or a chlorine or bromine atom or a methyl or ethyl group in the 8 or 9 position of the heterocycle, or $X^1$ and $X^2$ represent =CH— groups and B represents the divalent group (U), wherein $R^8$ is a hydrogen atom and $R^9$ is a methyl group, or the group (V), wherein at least one of the groups $R^3$ and $R^4$ is a hydrogen atom, A is a two- to four- membered alkylene chain in the 3 or 4 position of the saturated heterocyclic ring, Z is a methylene group and $R^1$ and $R^2$ represent alkyl groups with 1 to 4 carbon atoms or together with the intermediate nitrogen atom represent the 1-pyrrolidinyl, 1-piperidinyl, 4-morpholinyl or hexahydro-1H-1-azepinyl group.

The compounds of general formula I may, after reaction with inorganic or organic acids, also occur in the form of their physiologically acceptable salts. Suitable acids include, for example, hydrochloric, hydrobromic, sulphuric, methylsulphuric, phosphoric, tartaric, fumaric, citric, maleic, succinic, gluconic, malic, p-toluenesulphonic, methanesulphonic and amidosulphonic acid.

To illustrate the object of the invention, the following compounds may be mentioned by way of example:

6,11-dihydro-11-[[3-[3-(1-piperidinyl)propyl]-1-piperidinyl]-carbonyl]-5H-pyrido[2,3-b][1,5]benzodiazepin-5-one 11-[[3-[2-(cyclopentylmethylamino)ethyl]-1-piperidinyl]-carbonyl-6,11-dihydro-5H-pyrido[2,3-b][1,5]benzodiazepin-5-one 6,11-dihydro-11-[[3-[3-(1-pyrrolidinyl)propyl]-piperidinyl]carbonyl]-5H-pyrido[2,3-b][1,5]benzodiazepin-5-one 6,11-dihydro-11-[[3-[2-(hexahydro-1H-1-azepinyl)ethyl]1-piperidinyl]-carbonyl]-5H-pyrido[2,3-b][1,5]benzodiazepin-5-one-methanesulphonate D,L-6,11-dihydro-11-[[3-[2-(1-piperidinyl)ethyl]-1-piperidinyl]carbonyl]-5H-pyrido[2,3-b][1,5]benzodiazepin-5-one (+)-6,11-dihydro-11-[[3-[2-(1-piperidinyl)ethyl]-1-piperidinyl]carbonyl]-5H-pyrido[2,3-b][1,5]benzodiazepin-5-one (−)-6,11-dihydro-11-[[3-[2-(1-piperidinyl)ethyl]-1-piperidinyl]carbonyl]-5H-pyrido[2,3-b][1,5]benzodiazepin-5-one 11-[[3-[2-(diethylamino)ethyl]-1-piperidinyl]carbonyl]-6,11-dihydro-5H-pyrido[2,3-b][1,5]benzodiazepin-5-one 11-[[3-[3-(diethylamino)propyl]-1-piperidinyl]carbonyl]-6,11-dihydro-5H-pyrido[2,3-b][1,5]benzodiazepin-5-one 6,11-dihydro-11-[[4-[4-(1-pyrrolidinyl)butyl]-1-piperidinyl]-carbonyl]-5H-pyrido[2,3-b][1,5]benzodiazepin-5-one-hydrochloride 6,11-dihydro-11-[[3-[3-(4-morpholinyl)propyl]-1-piperidinyl]-carbonyl]-5H-pyrido[2,3-b][1,5]benzodiazepin-5-one 11-[[2-[[[3-(diethylamino)propyl]methylamino]methyl]-1-piperidinyl]carbonyl]-6,11-dihydro-5H-pyrido[2,3-b]-1,5]benzodiazepin-5-one-dihydrochloride 11-[[2-[2-[[3-(diethylamino)propyl]methylamino]ethyl]-1-piperidinyl]carbonyl]-6,11-dihydro-5H-pyrido[2,3-b][1,5]-benzodiazepin-5-one 6,11-dihydro-11-[[3-[3-(1-piperidinyl)propyl]-1pyrrolidinyl]-carbonyl]-5H-pyrido[2,3-b][1,5]benzodiazepin-5-one 6,11-dihydro-11-[[3-[3-(1-piperidinyl)propyl]-hexahydro-1H-1-azepinyl]carbonyl]-5H-pyrido[2,3-b][1,5]benzodiazepin-5-one 11-[[3-[2-[(cyclopentyl)ethylamino]ethyl]-1-pyrrolidinyl]carbonyl]-6,11-dihydro-5H-pyrido[2,3-b][1,5]-benzodiazepin-5-one 11-[[3-[2-[(cyclobutylmethyl)methylamino]ethyl]-1-pyrrolidinyl]carbonyl]-6,11-dihydro-5H-pyrido[2,3-b][1,5]-benzodiazepin-5-one 6,11-dihYdro-11-[[3-[4-(1-pyrrolidinyl)butyl]-1pyrrolidinyl]-carbonyl]-5H-pyrido[2,3-b][1,5]benzodiazepin-5-one 6,11-dihydro-11-[[3-[2-(1-pyrrolidinyl)ethyl]-hexahydro-1H-1-azepinyl]carbonyl]-5H-pyrido[2,3-b][1,5]benzodiazepin-5-one 6,11-dihydro-11-[[3-[2-(hexahydro-1H-1-azepinyl)ethyl]-pyrrolidinyl]carbonyl]-5H-pyrido[2,3-b][1,5]benzodiazepin-5-one 6,11-dihydro-11-[[3-[2-(hexahydro-1H-1-azepinyl)ethyl]-hexahydro-1H-1-azepinyl]carbonyl]-5H-pyrido[2,3-b]1,5]benzodiazepin-5-one 11-[[3-[2-(diethylamino)ethyl]-1-pyrrolidinyl]carbonyl]6,11-dihydro-5H-pyrido[2,3-b][1,5]benzodiazepin-5-one 11-[[3-[2-(diethylamino)ethyl]hexahydro-1H-1-azepinyl]carbonyl]-6,11-dihydro-5H-pyrido[2,3-b][1,5]benzodiazepin-5-one 6,11-dihydro-11-[[3-[4-(dimethylamino)butyl]-1-piperidinyl]-carbonyl]-5H-pyrido[2,3-b][1,5]benzodiazepin-5-one 11-[[3-[2-(butylethylamino)ethyl]-1-piperidinyl]carbonyl]-6,11-dihydro-5H-pyrido[2,3-b][1,5]benzodiazepin-5-one 6,11-dihydro-11-[[3-[3-(dipropylamino1propyl]-1-piperidinyl]-carbonyl]-5H-pyrido[2,3-b][1,5]benzodiazepin-5-one 11-[[3-[2-(dibutylamino)ethyl]-1-piperidinyl]carbonyl]-6,11-dihydro-5H-pyrido[2,3-b][1,5]benzodiazepin-5-one 6,11-dihydro-11-[[3-[[(1-methyl-4-piperidinyl)methylamino]methyl-1-piperidinyl]carbonyl]-5H-pyrido[2,3-b]1,5]benzodiazepin-5-one 6,11-dihydro-11-[[2-[[(1-methyl-4-piperidinyl)methylamino]methyl]-4-morpholinyl]carbonyl]-5H-pyrido[2,3-b][1,5]-benzodiazepin-5-one 6,11-dihydro-11-[[4-[3-(1-piperidinyl)propyl]-1-piperidinyl]-carbonyl]-5H-pyrido[2,3-b][1,5]benzodiazepin-5-one 11-[[4-[3-(diethylamino)propyl]-1-piperidinyl]carbonyl]-6,11-dihydro-5H-pyrido[2,3-b][1,5]benzodiazepin-5-one 11-[[4-[4-(diethylamino)butyl]-1-piperidinyl]carbonyl]-6,11-dihydro-5H-pyrido[2,3-b][1,5]benzodiazepin-5-one 5,11-dihydro-11-[[4-[3-(1-piperidinyl)propyl]-1-piperidinyl]carbonyl]-6H-pyrido[2,3-b][1,4]benzodiazepin-6-one 5,11-dihydro-11-[[3-[3-(1-piperidinyl)propyl]-1-piperidinyl]-carbonyl]-6H-pyrido[2,3-b][1,4]benzodiazepin-6-one 5,11-dihydro-11-[[4-[4-(1-piperidinyl)butyl]-1-piperidinyl]-carbonyl]-6H-pyrido[2,3-b][1,4]benzodiazepin-6-one 11-[[3-[2-[(cyclopentyl)methylamino]ethyl]-1-piperidinyl]carbonyl]-5,11-dihydro-6H-pyrido[2,3-b][1,4]benzodiazepin-6-one 5,11-dihydro-11-[[3-[3-(1-pyrrolidinyl)propyl]-1-piperidinyl]-carbonyl]-6H-pyrido[2,3-b][1,4]benzodiazepin-6-one 5,11-dihydro-11-[[4-[4-(1-pyrrolidinyl)butyl]-1-piperidinyl]-carbonyl]-6H-pyrido[2,3-b][1,4]benzodiazepin-6-one 5,11-dihydro-11-[[3-[4-(1-pyrrolidinyl)butyl]-1-piperidinyl]-carbonyl]-6H-pyrido[2,3-b][1,4]benzodiazepin-6-one 5,11-dihydro-11-[[3-[3-(1-pyrrolidinyl)propyl]-hexahydro-1H-1-azepinyl]carbonyl]-6H-pyrido[2,3-b][1,4]-benzodiazepin-6-one (+)-5,11-dihydro-11-[[3-[2-(1-piperidinyl)ethyl]-1-piperidinyl]carbonyl]-6H-pyrido[2,3-b][1,4]benzodiazepin-6-one (−)-5,11-dihydro-11-[[3-[2-(1-piperidinyl)ethyl]-1-piperidinyl]carbonyl]-6H-pyrido[2,3-b][1,4]benzodiazepin-6-one 5,11-dihydro-11-[[3-[2-(hexahydro-1H-1-azepinyl)ethyl]-1-piperidinyl]carbonyl]-6H-pyrido[2,3-b][1,4]benzodiazepin-6-one-methanesulphonate 11-[[3-[2-(diethylamino)ethyl]-1-piperidinyl]carbonyl]-5,11-dihydro-6H-pyrido[2,3-b][1,4]benzodiazepin-6-one 11-[[3-[3-(diethylamino)propyl]-1-piperidinyl]carbonyl]-5,11-dihydro-6H-pyrido[2,3-b][1,4]benzodiazepin-6-one 11-[[2-[3-(diethylamino)propyl]-4-morpholinyl]carbonyl]-5,11-dihydro-6H-pyrido[2,3-b][1,4]benzodiazepin-6-one 11-[[4-[3-(diethylamino)propyl]-1-piperidinyl]carbonyl]-5,11-dihydro-6H-pyrido[2,3-b][1,4]benzodiazepin-6-one 8-chloro-5,11-dihydro-11-[[3-[2-(1-piperidinyl)ethyl]-1-piperidinyl]carbonyl]-6H-pyrido[2,3-b][1,4]benzodiazepin-6-one 9-chloro-5,11-dihydro-11-[[3-[2-(1-piperidinyl)ethyl]-1-piperidinyl]carbonyl]-6H-pyrido[2,3-b][1,4]benzodiazepin-6-one 5,11-dihydro-8-methyl-11-[[3-[2-(1-piperidinyl)ethyl]-1-piperidinyl]carbonyl]-6H-pyrido[2,3-b][1,4]benzodiazepin-6-one 5,11-dihydro-8-ethyl-11-[[3-[2-(1-piperidinyl)ethyl]-1-piperidinyl]carbonyl]-6H-pyrido[2,3-b][1,4]benzodiazepin-6-one 5,11-dihydro-9-methyl-11-[[3-[2-(1-piperidinyl)ethyl]-1-piperidinyl]carbonyl]-6H-pyrido[2,3-b][1,4]benzodiazepin-6-one 5,11-dihydro-11-[[3-[3-(4-morpholinyl)propyl]-1-piperidinyl]carbonyl]-6H-pyrido[2,3-b][1,4]benzodiazepin-6-one 11-[[2-[[[3-(diethylamino)propyl]methylamino]methyl]-1-piperidinyl]carbonyl]-5,11-dihydro-6H-pyrido[2,3-b][1,4]-benzodiazepin-6-one-dihydrochloride 5,11-dihydro-11-[[3-[2-(dipropylamino)ethyl]-1-piperidinyl]carbonyl]-6H-pyrido[2,3-b][1,4]benzodiazepin-6-one-hydrochloride 5,11-dihydro-11-[[3-[2-[(2-methylpropyl)methylamino]ethyl]-1-piperidinyl]carbonyl]-6H-pyrido[2,3-b][1,4]benzodiazepin-6-one-hydrochloride 5,11-dihydro-11-[[3-[2-[(methylethyl)methylamino]ethyl]-1-piperidinyl]carbonyl]-6H-pyrido[2,3-b][1,4]benzodiazepin-6-one 5,10-dihydro-5-[[3-[2-(1-piperidinyl)ethyl]-1-piperidinyl]carbonyl]-11H-dibenzo[b,e][1,4]diazepin-11-one 6-chloro-5,10-dihydro-5-[[3-[2-(1-piperidinyl)ethyl]-1-piperidinyl]carbonyl]-11H-dibenzo[b,e][1,4]diazepin-11-one 4,9-dihydro-3-methyl-4-[[3-[2-(1-piperidinyl)ethyl]-1-piperidinyl]carbonyl]-10H-thieno[3,4-b][1,5]benzodiazepin-10-one 1,3-dimethyl-4-[[3-[4-(1-piperidinyl)butyl]-1-piperidinyl]carbonyl]-1,4,9,10-tetrahydropyrrolo[3,2-b][1,5]benzodiazepin-10-one 3-chloro-1-methyl-4-[[3-[4-(1-piperidinyl)butyl]-1-piperidinyl]carbonyl]-1,4,9,10-tetrahydropyrrolo[3,2-b][1,5]benzodiazepin-10-one 1-methyl-4-[[3-[4-(1-piperidinyl)butyl]-1-piperidinyl]carbonyl]-1,4,9,10-tetrahydropyrrolo[3,2-b][1,5]benzodiazwpin-10-one 4-[[3-[3-(diethylamino)propyl]-1-piperidinyl]carbonyl]-1,3-dimethyl-1,4,9,10-tetrahydropyrazolo[4,3-b][1,5]benzodiazepin-10-one 4-[[3-[3-(diethylamino)propyl]-1-piperidinyl]carbonyl]-1-methyl-1,4,9,10-tetrahydropyrazolo[4,3-b][1,5]benzodiazepin-10-one 4-[[3-[3-(diethylamino)propyl]-1-piperidinyl]carbonyl]-1-methyl-1,4,9,10-tetrahydropyrazolo[4,3-e]pyrido[3,2-b][1,4]diazepin-10-one.

According to the invention, the new base substituted condensed diazepinones of general formula I are obtained by the following processes:

a) Base substituted condensed diazepinones of general formula Ia

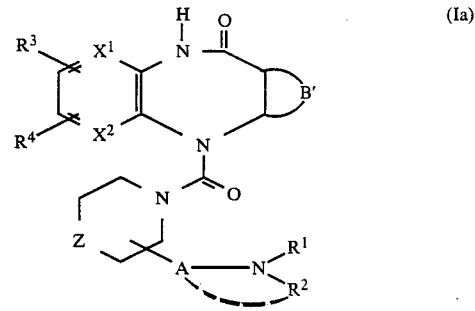

(Ia)

wherein $R^1$, $R^2$, $R^3$, $R^4$, $X^1$, $X^2$, A and Z are defined as hereinbefore and B' represents one of the divalent groups (S), (U), (V), (W) or (T')

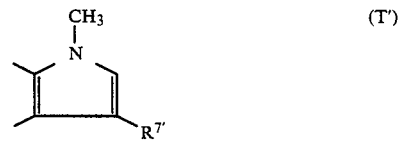

(T')

wherein $R^{7'}$ is a chlorine atom or a methyl group, are obtained by reacting carbonic acid derivatives of general formula II

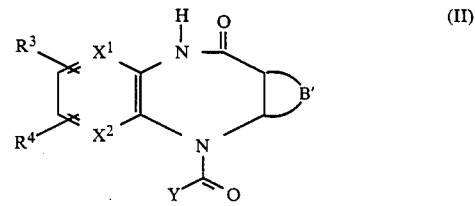

(II)

wherein $R^3$, $R^4$, B', $X^1$ and $X^2$ are as hereinbefore defined and Y represents a halogen atom, preferably bromine or chlorine, or the group $OR^{11}$, wherein $R^{11}$ represents an optionally halogen-substituted alkyl group with 1 to 5 carbon atoms, a phenyl group optionally substituted by halogen atoms or nitro groups or an aralkyl group with 7 to 15 carbon atoms, with compounds of general formula III

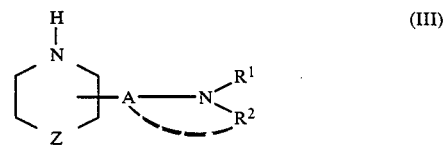

(III)

wherein $R^1$, $R^2$, A and Z are as hereinbefore defined.

The reaction is carried out without or preferably in the presence of solvents such as water, toluene or alcohols such as methanol, ethanol or isopropanol, but preferably in the presence of aprotic polar solvents, e.g. tetrahydrofuran, 1,4-dioxan, acetonitrile, N,N-dimethylformamide, dimethylsulphoxide, hexamethylphosphoric acid triamide, or mixtures thereof and at temperatures between $-10°$ C. and the boiling point of the reaction mixture, preferably between 40° and 100° C. It has proved satisfactory to use additional inorganic or organic bases, e.g. alkaline or alkaline-earth metal hydroxides, alkoxides or carbonates, e.g. sodium hydroxide, sodium methoxide, potassium tert.butoxide, sodium carbonate and potassium carbonate; tertiary amines, such as triethylamine, ethyl diisopropylamine, N,N-dimethylaniline, pyridine or 4-(dimethylamino)pyridine; it is also advantageous to carry out the reaction in the presence of an excess of a compound of general formula III.

If the amines of general formula III and the carbonic acid derivatives of general formula II are used in equimolar amounts, and provided that Y represents a halogen atom, the hydrohalic acid salts of the desired compounds of general formula Ia are obtained directly.

However, the reaction may also be carried out with a metal compound of general formula IIIa

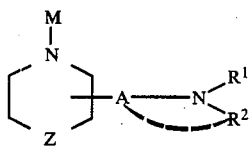
(IIIa)

wherein M represents an alkali metal atom or one equivalent of an alkaline earth metal atom. Metal compounds of general formula IIIa may readily be prepared in situ from III by reacting with alkali or alkaline earth metals, e.g. sodium, potassium or barium, or with alkali or alkaline earth metal hydrides, e.g. sodium, potassium or calcium hydride, or by reacting with alkali or alkaline earth organometallic compounds, e.g. with n-butyllithium or phenyllithium.

(b) Base substituted condensed diazepinones of general formula Ia may also be obtained by reacting tricyclic compounds of general formula IV;

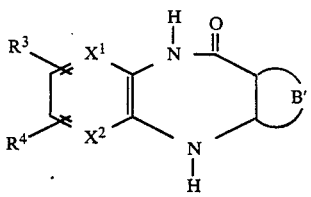
(IV)

wherein the groups $R^3$, $R^4$, $X^1$, $X^2$ and B' are as hereinbefore defined, with a chlorocarbonic acid derivative of general formula V

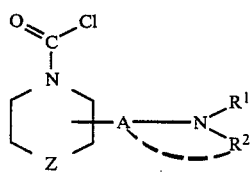
(V)

wherein the groups $R^1$, $R^2$, A and Z are as hereinbefore defined.

The reaction is preferably carried out in inert organic solvents, for example in aromatic hydrocarbons such as toluene or xylene, in ethers such as diisopropylether, tetrahydrofuran or dioxan, in ketones such as 3-pentanone, in chlorinated aliphatic hydrocarbons such as 1,2-dichloroethane or in other solvents such as acetonitrile or dimethylformamide or in mixtures thereof, optionally in the presence of tertiary organic bases such as pyridine and at temperatures up to the boiling point of the reaction mixture, preferably at temperatures of between +30° and +100° C.

(c) The new pyrrolo-condensed diazepinones of general formula Ib

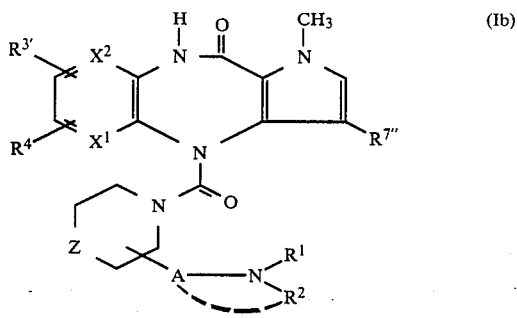
(Ib)

(wherein $R^1$, $R^2$, $R^4$, $X^1$, $X^2$, A and Z have the meanings hereinbefore defined, with the exception for Z of a sulphur atom, $R^{7''}$ represents a hydrogen atom and $R^{3'}$ represents an alkyl group with 1 to 4 carbon atoms or a hydrogen atom), which come under general formula I, may also be prepared by hydrogenolysis from compounds of general formula Ib wherein $R^{7''}$ represents a chlorine atom.

The hydrogenolysis is carried out in the presence of catalysts of metals of the VIIIth sub-group of the periodic table of elements, for example palladium on animal charcoal, palladium on barium sulphate, Raney nickel or Raney cobalt, and under hydrogen pressures of from 1 to 300 bar and temperatures of 0° C. to 130° C. in the presence of solvents, e.g. alcohols such as methanol or ethanol; ethers such as dioxan, tetrahydrofuran; carboxylic acids, for example acetic acid; or tertiary amines, for example triethylamine. If the process is carried out in the absence of additional hydrogen chloride acceptors, for example sodium carbonate, potassium hydrogen carbonate, triethylamine or sodium acetate, the hydrochlorides of the desired compounds are obtained directly and may be isolated after removal of the catalyst by evaporation of the reaction solution. If in the above-mentioned hydrogenolysis reaction the hydrogen is replaced by formic acid, the reaction will in principle take place even under unpressurised conditions. In this variant, it has proved particularly useful to carry out the reaction with formic acid in the presence of dimethylformamide as solvent and palladium on charcoal as catalyst at temperatures of between 70° and 110° C. and to carry out the reduction with triethylammonium formate in the presence of excess triethylamine and palladium on animal charcoal or palladium acetate and triarylphosphines such as triphenylphosphine, tris-(o-tolyl)phosphine, tris-(2,5-diisopropylphenyl)phosphine, at temperatures of between 40° and 110° C.

Bases of general formula I thus obtained may subsequently be converted into the acid addition salts thereof or, if acid addition salts are obtained, they may be converted into the free bases or other pharmacologically acceptable acid addition salts.

The aminoacylated condensed diazepinones of general formula I according to the invention contain, in some instances, an asymmetric carbon atom in the side chain. These compounds may therefore occur as enantiomeric (+) and (−) forms. The invention includes the individual isomers and their racemates.

The separation of any racemates of the compounds of general formula I may be carried out by known methods, for example using an optically active acid such as (+) or (−) tartaric acid or a derivative thereof such as (+) or (−) diacetyltartaric acid, (+) or (−) monomethyltartrate or (+) camphorsulphonic acid.

According to a conventional method of isomer separation, the racemate of a compound of general formula I is reacted in equimolar amounts with one of the above-mentioned optically active acids in a solvent and the crystalline diastereomeric salts obtained are separated by making use of their different solubilities. This reaction may be carried out in any type of solvent provided that it shows sufficient differences in solubility of the salts. Preferably, methanol, ethanol or mixtures thereof are used, e.g. in a ratio by volume of 50:50. Each of the diastereomeric salts is then dissolved in water, neutralised with a base such as sodium hydroxide or potassium hydroxide and in this way the corresponding free compound is obtained in the (+) or (−) form.

Only one enantiomer is obtained if the methods of synthesis described above are carried out with only one enantiomer of general formula III or V.

The carbonic acid derivatives of general formula II required as intermediate products are obtained, analogously to DE-A-No. 32 04 169, DE-A-No. 32 04 158 and DE-A-No. 32 04 401, by reacting tricyclic compounds of general formula IV

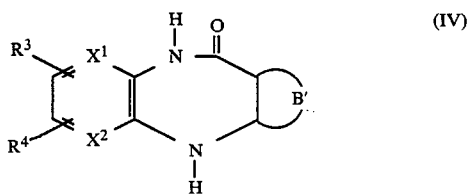
(IV)

wherein the groups $R^3$, $R^4$, $X^1$, $X^2$ and B' are as hereinbefore defined, with a halocarbonic acid derivative of general formula VI

(IV)

wherein Hal represents the bromine or chlorine atom, preferably the chlorine atom, and Y is as hereinbefore defined.

The reaction is carried out in inert organic solvents, for example aromatic hydrocarbons, such as toluene, chlorobenzene or xylene; open-chained or cyclic ethers such as diisopropylether, tetrahydrofuran or dioxan; open-chained or cyclic aliphatic ketones, for example 3-pentanone; chlorinated aliphatic hydrocarbons such as 1,2-dichloroethane or other solvents such as acetonitrile or dimethylformamide or in mixtures thereof and preferably in the presence of tertiary organic bases, preferably pyridine, and at temperatures up to, at most, the boiling point of the solvent or mixture of solvents used, preferably between +30° and +80° C.

Intermediate compounds of general formula III which have an alkylene group A interrupted in the β-position relative to the saturated heterocycle by a heteroatom may be synthesised analogously to the methods discussed in detail in DE-A-No. 36 26 095.

Intermediate compounds of general formula III wherein Z represents a methylene group are conveniently prepared from correspondingly substituted pyridines, for example by catalytic hydrogenation in ethanolic/hydrochloric acid solution and using platinum(IV) oxide as catalyst (see also F. F. Blicke et al., J. Org. Chemistry 26, 3258 (1961)) or in glacial acetic acid and in the presence of platinum(IV)oxide (see also W. F. Minor et al., J. Med. Pharm. Chem. 5, 96, 105 ff. (1962) and A. H. Sommers et al., J. Amer. Chem. Soc. 75, 57, 58 ff. (1953)). The substituted pyridines may in turn easily be synthesised by methods familiar to those skilled in the art, e.g. by the addition of corresponding secondary amines, dialkylaminoalkanols or dialkylaminoalkanethiols to vinyl pyridines, by reduction of suitable pyridine alkanoic acid amides with lithium aluminium hydride, by alkylation of picolines with dialkylaminoalkylhalides in the presence of lithium diisopropylamide or sodium amide (see also A. E. Tschitschibabin, Bull. Soc. Chim. France 1938, 436) or by reacting (omega-haloalkyl)-pyridines with dialkylaminoalkanols, dialkylaminoalkanethiols or secondary amines (see also L. Rondahl, Acta Pharm. Suec. 13, 229–34 (1976)) or the metallised derivatives thereof.

A generally applicable method of synthesising amines of general formula III consists in reducing suitable heterocyclically substituted alkane carboxylic acid dialkylamides which are optionally interrupted by heteroatoms in the alkylene group, for example using lithium aluminium hydride. Any protecting groups still present from the preliminary stages and occurring on the nitrogen function of the saturated heterocycle may subsequently be split off in the usual way; a benzyl group may, for example, be split off by hydrogenolysis in the presence of palladium/animal charcoal. For example, 5-oxo-2-pyrrolidine acetic acid (G. L. Evans et al., J. Amer. Chem. Soc., 72, 2727 (1950)) may be reacted successively with thionyl chloride and a dialkylamine of interest and the resulting N,N-dialkyl-5-oxo-2-pyrrolidinoacetamide may subsequently be reduced with lithium aluminium hydride to yield the desired 2-[2-(dialkylamino)-ethyl]pyrrolidine; or the 4-benzyl-3-(chloromethyl)-morpholine hydrochloride obtainable from 4-benzyl-3-(hydroxymethyl)-morpholine (G. R. Brown et al., J. Chem. Soc. Perkin Trans. I 1985, 2577) by the action of thionyl chloride may be converted into (4-benzyl-3-morpholinyl)alkanoic acids by chain lengthening in the usual way and thus be used for the synthesis of 3-(dialkylaminoalkyl)morpholines.

The tricyclic compounds of general formula IV are known from the patent literature or may be synthesised from available starting materials by adhering closely to published methods.

Halocarbonic acid derivatives of general formula VI are known.

The invention further relates to pharmaceutical compositions which contain one or more base substituted diazepinones of general formula I or the physiologically acceptable salts thereof.

For this purpose, the compounds of general formula I may be incorporated, in known manner, in the conventional pharmaceutical preparations, e.g. solutions, suppositories, tablets, coated tablets, capsules or infusions. The daily dosage is generally between 0.01 and 5 mg/kg, preferably 0.02 and 2.5 mg/kg, more particularly 0.05 and 1.0 mg/kg of body weight, preferably administered in the form of several, preferably 1 to 3, individual doses, to achieve the desired results.

The base substituted condensed diazepinones of general formula I and the acid addition salts thereof have valuable properties; in particular, they have favorable effects on heart rate and, owing to their lack of mydriatic effects and inhibitory effects on gastric acid secretion and salivation, they are suitable for use as vagal pacemakers for treating bradycardia and bradyarrhythmia in human and veterinary medicine; some of the compounds also have spasmolytic properties on peripheral organs, particularly the colon and bladder.

A favorable relation between tachycardiac effects on the one hand and on the other hand the undesirable effects on pupil size and the secretion of tears, saliva and gastric acid which occur in therapeutic agents with an anticholinergic component is of particular importance in the therapeutic use of the substances. The following tests show that the compounds according to the invention show surprisingly good relations of this kind.

A. Investigation of functional selectivity of the antimuscarinic effect

Substances with antimuscarinic properties inhibit the effects of agonists supplied exogenically or of acetylcholine, which is released from cholinergic nerve endings. The following is a description of some methods used to detect cardioselective antimuscarinic agents.

"In vitro" organ preparations

Dissociation constants ($K_B$ values) were determined "in vitro" on the ileum and spontaneously beating atrium of the guinea pig. The ileum was taken out and incubated in Krebs-Henseleit solution in an organ bath. Contractions were induced by increasing concentrations of methacholine (M) so that total concentration/activity curves could be recorded. M was then washed out, the test substance was added and kept in contact for 30 minutes and another concentration/activity curve was recorded with M.

The dosage ratio (DR), i.e. the extent of displacement of the concentration/activity curve, was used to calculate the dissociation constant according to Arunlakshana and Schild (Brit. J. Pharmacol. 14, 48, 1959).

M had a concentration-dependent heart rate reducing effect on the isolated, spontaneously beating, right atrium. This effect was cancelled out by the addition of an antimuscarinic. Dissociation constants for the muscarinic receptors of the atrium were obtained in the manner described above. Comparison of the dissociation constants obtained in two tissues made it possible to identify cardioselective substances. The results are contained in Table III.

"In vivo" methods

The objective of the methods was to confirm the selectivity of the antimuscarinic effect. Those substances which had been selected on the basis of "in vitro" tests were tested for their
1. $M_1/M_2$ selectivity in the rat,
2. Salivation-inhibiting effect on the rat and
3. Inhibition of the acetylcholine effect on the bladder, bronchi and heart rate in the guinea pig.

1. $M_1/M_2$ selectivity in the rat

The method used was described by Hammer and Giachetti (Life Sciences 31, 2991–2998 (1982)). 5 minutes after the intravenous injection of increasing doses of the substance, either the right vagus was electrically stimulated (frequency: 25 Hz; pulse width: 2 ms; duration of stimulus: 30 s; voltage: supramaximal) or 0.3 mg/kg of McN-A-343 were intravenously injected into male THOM rats. The bradycardia caused by vagus stimulation and the rise in blood pressure caused by McN-A-343 were determined. The dosage of the substances which reduced either the vagal bradycardia ($M_2$) or the rise in blood pressure ($M_1$) by 50% was determined graphically. For the results see Table II.

2. Salivation-inhibiting effect in the rat

Using the method of Lavy and Mulder (Arch. int. Pharmacodyn. 178, 437–445, (1969)) male THOM rats anaesthetised with 1.2 g/kg of urethane were given increasing doses of the substance by i.v. route. The secretion of saliva was initiated by subcutaneous administration of 2 mg/kg of pilocarpine. The saliva was absorbed with blotting paper and the surface area covered was measured every 5 minutes by planimetry. The dosage of the substance which reduced the volume of saliva by 50% was determined graphically. For the results see Table II.

3. Inhibition of the effect of acetylcholine on the bladder, bronchi and heart rate in guinea pigs 5 minutes after the administration of the test substance, 10 mcg/kg of acetylcholine were simultaneously injected intravenously and intra-arterially into anaesthetised guinea pigs. The heart rate was recorded directly by extracorporeal derivation of the ECG, the expiration resistance according to Konzett-Rössler and contraction of the exposed bladder. In order to determine the inhibition of the acetylcholine activity on the organs under investigation, dosage/activity curves were recorded and from them $-\log ED_{50}$ values were determined. For the results see Table V.

B Studies of binding to muscarinic receptors:

(1) In vitro: Measurement of the $IC_{50}$ value

The organs were donated by male Sprague-Dawley rats weighing 180–220 g. After the heart and submandibular gland had been removed, all other steps were carried out in ice cold Hepes HCl buffer (pH 7.4; 100 mmolar NaCl, 10 mmolar $MgCl_2$). The whole heart was cut up with scissors. All the organs were then homogenised in a Potter apparatus.

For the binding test the homogenised organs were diluted as follows:

| Whole heart | 1:400 |
|---|---|
| Submandibular gland | 1:400 |

The homogenised organs were incubated at a certain concentration of the radioligand and at a series of concentrations of the non-radioactive test substances in an Eppendorf centrifuge tube at 30° C. Incubation lasted 45 minutes. The radioligand used was 0.3 nmolar $^3$H-N-methylscopolamine ($^3$H-NMS). Incubation was ended by the addition of ice cold buffer followed by vacuum filtration. The filters were rinsed with cold buffer and their radioactivity was determined. It represents the sum of specific and non-specific binding of $^3$H-NMS The proportion of non-specific binding was defined as the radioactivity, which was bound in the presence of 1 micromolar quinuclidinylbenzylate. Each measurement was taken four times. The $IC_{50}$ values of the non-labelled test substances were determined graphically.

They represent that concentration of test substance at which the specific binding of $^3$H-NMS to the muscarinic receptors in the various organs was inhibited by 50%. The results can be seen from Table 1.

(2) In vivo: Determination of ID$_{50}$ values

For these experiments, female rats with a body weight of about 200 g were used. Before the start of the experiment the animals were anaesthetised with a dose of 1.25 g/kg of urethane. The animals were given the dosage of test substance by i.v. injection. After 15 minutes, 113 ng/kg of $^3$H-N-methylscopolamine ($^3$H-NMS) were given by the same route. After another 15 minutes the animals were killed and their heart, bronchi and lachrymal glands were taken out. These organs were dissolved in Soluene R and the radioactivity was measured. These measurements were taken as representing total binding. The proportion of non-specific binding was defined as the radioactivity which could not be suppressed by the administration of 2 mg/kg of atropine. The ID$_{50}$ values for the individual organs were determined from these experiments. The ID$_{50}$ values are the dosages of test substances which inhibited 50% of specific binding of $^3$H-NMS to the muscarinic receptors of the particular organs. The results appear in Table IV.

The following compounds for example were investigated as described above:

A=5,11-dihydro-11-[[3-[3-(1-piperidinyl)propyl]-1-piperidinyl]carbonyl]-6H-pyrido[2,3-b][1,4]-benzodiazepin-6-one B=5,11-dihydro-11-[[3-[3-(1-pyrrolidinyl)propyl]-1-piperidinyl]carbonyl]-6H-pyrido[2,3-b][1,4]benzodiazepin-6-one-hydrochloride C=5,11-dihydro-11-[[3-[2-(1-piperidinyl)ethyl]-1-piperidinyl]carbonyl]-6H-pyrido[2,3-b][1,4]benzodiazepin-6-one-methanesulphonate D=5,11-dihydro-11-[[3-[2-(1-pyrrolidinyl)ethyl]-1-piperidinyl]carbonyl]-6H-pyrido[2,3-b][1,4]benzodiazepin-6-one-hydrochloride E=11-[[3-[2-[(cyclopentyl)methylamino]ethyl]-1-piperidinyl]carbonyl]-5,11-dihydro-6H-pyrido[2,3-b]-1,4]benzodiazepin-6-one-hydrochloride F=5,11-dihydro-11-[[3-[2-(hexahydro-1H-1-azepinyl)ethyl]-1-piperidinyl]carbonyl]-6H-pyrido[2,3-b][1,4]-benzodiazepin-6-one-hydrochloride G=6,11-dihydro-11-[[3-[2-(1-piperidinyl)ethyl]-1-piperidinyl]carbonyl]-5H-pyrido[2,3-b][1,5]benzodiazepin-5-one and as comparison substances X=11-[[2-[(diethylamino)methyl]-1-piperidinyl]acetyl]-5,11-dihydro-6H-pyrido[2,3-b][1,4]benzodiazepin-6-one (see U.S. Pat. No. 4 550 107)

Y=5,11-dihydro-11-[(4-methyl-1-piperazinyl)acetyl]-6H-pyrido[2,3-b][1,4]benzodiazepin-6-one (pirenzepine, see U.S. Pat. No. 3 660 380)

and

Z=atropine.

The following Tables show the results found:

TABLE I

| | Receptor binding tests in vitro: | | |
|---|---|---|---|
| | Receptor binding tests log IC$_{50}$[nM1$^{-1}$] | | Selectivity factor: ratio IC$_{50}$ |
| Substance | Heart | Submandibular gland | submandibular gland to IC$_{50}$ heart |
| A | 8.70 | 7.70 | 10 |
| B | 8.00 | 7.40 | 4 |
| C | 8.52 | 7.52 | 10 |
| D | 8.22 | 7.30 | 8.3 |

TABLE I-continued

| | Receptor binding tests in vitro: | | |
|---|---|---|---|
| | Receptor binding tests log IC$_{50}$[nM1$^{-1}$] | | Selectivity factor: ratio IC$_{50}$ |
| Substance | Heart | Submandibular gland | submandibular gland to IC$_{50}$ heart |
| E | 8.52 | 7.52 | 10 |
| F | 8.52 | 7.52 | 10 |
| G | 8.40 | 7.40 | 10 |
| X | 6.82 | 5.30 | 33 |
| Y | 5.82 | 6.70 | 0.13 |
| Z | 8.40 | 8.40 | 1 |

TABLE II

M$_1$/M$_2$ selectivity and salivation-inhibiting activity on the rat:

| Substance | M$_2$ activity (rat) ED$_{50}$[mcg/kg] i.v. | M$_1$ activity (rat) ED$_{50}$[mcg/kg] i.v. | Salivation inhibition (rat) ED$_{50}$[mcg/kg] i.v. | Ratio of salivation inhibition to M$_2$-activity |
|---|---|---|---|---|
| A | 6.9 | 49 | 35 | 5 |
| C | 7.6 | 39 | 58 | 7.6 |
| G | 8.13 | 7.16 | 6.83 | 20.00 |
| X | 160 | 988 | 4215 | 26.3 |
| Y | 883 | 40 | 84 | 0.1 |
| Z | 4 | 16 | 9 | 2.2 |

TABLE III

Dissociation constants (K$_B$ values) on the ileum and spontaneously beating atrium in the guinea pig:

| | K$_B$ [mol/l] | |
|---|---|---|
| Substance | Heart | Ileum |
| A | 3.47 × 10$^{-10}$ | 3.23 × 10$^{-9}$ |
| X | 1.05 × 10$^{-7}$ | 6.17 × 10$^{-7}$ |
| Y | 2.4 × 10$^{-7}$ | 1.55 × 10$^{-7}$ |
| Z | 1.41 × 10$^{-9}$ | 8.13 × 10$^{-10}$ |

TABLE IV

| | Receptor binding tests, in vivo: | | | | |
|---|---|---|---|---|---|
| | | | ID$_{50}$[mg/kg] | | Ratio of ID$_{50}$ in the lachrymal glands to ID$_{50}$ in the atrium |
| Substance | Atrium | Heart Ventricle | Bronchi | Lachrymal glands | |
| A | 0.01 | 0.005 | 0.06 | 0.2 | 20 |
| X | 1.0 | 0.6 | 15.0 | >30.0 | >30 |
| Y | 5.0 | 1.0 | 10.0 | 10.0 | 2 |
| Z | 0.08 | 0.03 | 0.1 | 0.2 | 1.5 |

TABLE V

Inhibition of acetylcholine activity on the bladder, bronchi and heart rate in the guinea pig: Results:

| | log ED$_{50}$[Mol kg$^{-1}$] | | |
|---|---|---|---|
| Substance | Heart | Bronchi | Bladder |
| A | 7.06 | 6.93 | 5.87 |
| B | 7.18 | 7.06 | 6.16 |
| C | 7.37 | 7.38 | 6.45 |
| D | 7.32 | 7.49 | 6.15 |
| E | 7.09 | 7.01 | 6.05 |
| F | 7.79 | 7.40 | 6.42 |
| G | 7.83 | 7.58 | 6.52 |
| X | 5.84 | 5.58 | 4.73 |
| Y | 5.85 | 6.57 | 5.36 |
| Z | 7.70 | 7.96 | 7.03 |

The information shown in Table I above shows that the new compounds of general formula I distinguish between muscarinic receptors in different tissues. This is clear from the substantially lower $IC_{50}$ values when the test substances are investigated on preparations from the heart compared with those from the submandibular gland.

The pharmacological data in Table II above shows—in total agreement with the receptor binding studies—that the heart rate is increased by the above-mentioned compounds even at dosages at which there is no restriction in the secretion of saliva. The ratio of the $ED_{50}$ in salivation inhibition to the $ED_{50}$ of the $M_2$ activity shows a sufficient safety gap from the side effect of dryness of the mouth for compounds A to G. This demonstrates ffectiveness (cf. Table IV), show adequate, therapeutically useful selectivity comparable with that of substance X.

Moreover, the pharmacological data in Table III above indicate a surprisingly high power of distinction between the heart and smooth muscle. A is significantly more effective than X and Y, and a clear selectivity in favour of the heart is apparent and compound A has significant advantages of efficacy over X and Y. Atropine (=Z) is a known non-selective anti-muscarinic and under these model conditions it shows an inverse selectivity ratio. The compounds mentioned are resorbed extremely well since they have a low dosage ratio p.o. to i.v. The smaller the ratio of $ED_{50}$p.o. to $ED_{50}$i.v., the better the resorption of the active substance.

Table IV shows the preferential binding to receptors of the heart (atrium/ventricle). Substance A shows a significant improvement in potency compared with substances X and Y on the heart. This is an important therapeutic advantage in the provision of a vagal pacemaker. This increase in effectiveness is achieved while retaining the useful selectivity gap from the effects on the exocrine glands, as is clear from the ratio of the $ID_{50}$ values on the lachrymal glands to the $ID_{50}$ values on the atrium. Atropine (=Z) on the other hand is not selective.

Moreover, the compounds prepared according to the invention are well tolerated; even in the highest doses administered, no toxic side effects were observed in the pharmacological trials.

All the substances of general formula I are characterised by exceptional resistance to hydrolysis. Consequently, it is possible to produce solutions for parenteral administration which will withstand long storage.

The Examples which follow are intended to illustrate the invention:

"M.p." indicates "melting point", "D." indicates "decomposition". Satisfactory elemental analyses by IR, UV, $^1$H-NMR and in many cases mass spectrometry have been obtained for all the compounds. Unless otherwise expressly stated, the percentages are always percent by weight.

EXAMPLE 1

5,11-Dihydro-11-[3-[3-(1-piperidinyl)propyl]-1-piperidinyl]carbonyl]-6H-pyrido[2,3-b][1,4]benzodiazepin6-one A solution of 2.00 g (9.51 mmol) of 3-[3-(1-piperidinyl)propyl]piperidine in 10 ml of dimethylformamide is added dropwise at ambient temperature and with stirring to a suspension of 2.6 g (9.50 mmol) of 11-(chlorocarbonyl)-5,11-dihydro-6H-pyrido[2,3-b][1,4]-benzodiazepin-6-one in 30 ml of dimethylformamide. The initially clear solution becomes cloudy within a few minutes. After half an hours' stirring at ambient temperature the colourless solid was removed by suction filtering and was washed thoroughly three times with 3 ml of ice cold ethanol. The colourless monohydrochloride of the desired compound obtained, m.p. >260° C., was dissolved in 10 ml of water, a saturated aqueous potassium carbonate solution was added until an obvious alkaline reaction occurred and the mixture was then filtered. The solid material obtained was thoroughly washed with water and then dried in a vacuum dryer at 50° C. and over di-phosphorous pentoxide. 3.0 g (71% of theory) of the desired 5,11-dihydro-11-[[3-[3-(1-piperidinyl)propyl]-1-piperidinyl]carbonyl]-6H-pyrido[2,3-b][1,4]benzodiazepin-6-one were obtained, m.p. 123°–125° C., Rf 0.41 (Merck DC ready made plates, silica gel 60 $F_{254}$; eluant: dichloromethane/methanol/ aqueous conc. ammonia 90/10/1, v/v/v)

To convert it into the hydrochloride, 500 mg of the base were dissolved in a mixture of 70 ml of ethyl acetate and 3 ml of ethanol and 1,12 ml of an ethereal 1-molar hydrogen chloride solution was added. The precipitate obtained was dissolved in a mixture of 50 ml of methanol and 2 ml of water, then evaporated down in vacuo to a total volume of 10 ml, and 30 ml of acetone were added. After trituration, colourless crystals were obtained which were dried and melted at above 260° C. The solubility in water was about 0.2%.

| $C_{26}H_{34}ClN_5O_2$ (484.04) | | | | | | | |
|---|---|---|---|---|---|---|---|
| Calc: | C | 64.52 | H | 7.08 | Cl | 7.32 | N | 14.47 |
| Found: | | 63.99 | | 7.13 | | 7.21 | | 14.35 |

300 mg of 5,11-dihydro-11-[[3-[3-(1-piperidinyl)-propyl]-1-piperidinyl]carbonyl]-6H-pyrido[2,3-b][1,4]-benzodiazepin-6-one were analogously dissolved in 100 ml of warm ethyl acetate and converted into the corresponding salt by treating with 60 mg of methanesulphonic acid. Colourless crystals, m.p. 183°–187° C., readily soluble in water.

| $C_{26}H_{33}N_5O_2 \cdot CH_3SO_3H$ (543.68) | | | | | | |
|---|---|---|---|---|---|---|
| Calc: | C | 59.65 | H | 6.86 | N | 12.88 | S | 5.90 |
| Found: | | 59.42 | | 6.75 | | 12.33 | | 5.91 |

The salt with N-cyclohexylsulphamidic acid melted at 204°–208° C. and was soluble in water, to about 1%.

| $C_{32}H_{46}N_6O_5S$ (611.80) | | | | | | |
|---|---|---|---|---|---|---|
| Calc: | C | 61.32 | H | 7.40 | N | 13.41 | S | 5.11 |
| Found: | | 60.83 | | 7.44 | | 13.08 | | 5.16 |

EXAMPLE 2

11-[[2-[2-(Diethylamino)ethyl]-1-piperidinyl]carbonyl]-5,11-dihydro-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[2-(diethylamino)ethyl]piperidine in a yield of 37% of theory. Colourless crystals, m.p. 100° C. (D.) (from acetonitrile), Rf 0.25 (Macherey-Nagel, Polygram® SIL G/UV$_{254}$, pre-coated plastic sheets for TLC; eluant: dichloromethane/,ethyl acetate/cyclohexane/methanol/conc. ammonia 57/25/8/8/1, v/v/v/v/v)

| $C_{24}H_{31}N_5O_2$ (421.54) | | | | | | |
|---|---|---|---|---|---|---|
| Calc: | C | 68.38 | H | 7.41 | N | 16.61 |
| Found: | | 68.18 | | 7.47 | | 16.80 |

EXAMPLE 3

5,11-Dihydro-11-[[2-[2-(dimethylamino)ethyl]-1-piperidinyl]-carbonyl]-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 2-[2-(dimethylamino)ethyl]piperidine in a yield of 37% of theory. Colourless crystals, m.p. 188°–190° C. (from acetonitrile), $R_f$ 0.6 (Macherey-Nagel, Polygram ® SIL G/UV$_{254}$, pre-coated plastic sheets for TLC; eluant: dichloromethane/cyclohexane/ methanol/conc. ammonia 68/15/15/2, v/v/v/v).

| $C_{22}H_{27}N_5O_2$ (393.49) | | | | | | |
|---|---|---|---|---|---|---|
| Calc: | C | 67.15 | H | 6.92 | N | 17.80 |
| Found: | | 66.97 | | 6.63 | | 17.83 |

EXAMPLE 4

11-[[2-[4-(Diethylamino)butyl]-1-pioeridinyl]carbonyl]-5,11-dihydro-6H-pyrido[2,3-b][1,4]benzodiazepin-6-one A mixture of 4.5 g (0.0164 mol) of 11-(chlorocarbonyl)-5,11-dihydro-6H-pyrido[2,3-b][1,4]bhenzodiazepin-6-one, 2.2 g (0.02 mol) of anhydrous sodium carbonate, 4.3 g (0.0202 mol) of 2-[4-(diethylamino)butyl]-piperidine and 100 ml of acetonitrile was refluxed for 1 hour with stirring. Then the solvent was distilled off in vacuo, the highly viscous residue remaining was taken up in 30 ml of water, made alkaline with sodium hydroxide and extracted exhaustively with dichloromethane. The combined dichloromethane phases were dried over sodium sulphate and evaporated down, the residue was purified chromatographically on silica gel (35–70 mesh) using dichloromethane/ethyl acetate/cyclohexane/methanol/conc. ammonia 58/25/8/8/1, v/v/v/v/v, as eluant. 4.0 g (56% of theory) of a colourless resin were obtained, which could not be crystallised.

| $C_{26}H_{35}N_5O_2$ (449.59) | | | | | | |
|---|---|---|---|---|---|---|
| Calc: | C | 69.46 | H | 7.85 | N | 15.58 |
| Found: | | 69.42 | | 7.96 | | 15.51 |

The water soluble dihydrochloride melted at 174°–175° C. (D.)

| $C_{26}H_{37}Cl_2N_5O_2$ (522.51) | | | | | | | | |
|---|---|---|---|---|---|---|---|---|
| Calc: | C | 59.77 | H | 7.14 | Cl | 13.57 | N | 13.40 |
| Found: | | 60.13 | | 7.07 | | 13.50 | | 13.45 |

EXAMPLE 5

5,11-Dihydro-11-[[2-[4-(dimethylamino)butyl]-1-piperidinyl]carbonyl]-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[4-(dimethylamino)butyl]piperidine in a yield of 55% of theory. Colourless crystals, m.p. 145°–147° C. (from ethyl acetate), $R_f$ 0.1 (Macherey-Nagel, Polygram ® SIL G/UV$_{254}$, pre-coated plastic sheets for TLC; eluant: dichloromethane/ethyl acetate/cyclohexane/methanol/conc. ammonia 58/25/8/8/1, v/v/v/v/v)

| $C_{24}H_{31}N_5O_2$ (421.54) | | | | | | |
|---|---|---|---|---|---|---|
| Calc: | C | 68.38 | H | 7.4 | N | 16.61 |
| Found: | | 68.40 | | 7.53 | | 16.45 |

EXAMPLE 6

11-[[2-[3-(Diethylamino)propyl]-1-piperidinyl]-carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[3-(diethylamino)propyl]piperidine in a yield of 70% of theory. Colourless crystals, m.p. 125°–128° C. (ethyl acetate), $R_f$ 0.15 (MachereyNagel, Polygram ® SIL G/UV$_{254}$, pre-coated plastic sheets for TLC; eluant: dichloromethane/ethyl acetate/cyclohexane/methanol/conc. ammonia 58/25/8/8/1, v/v/v/v/v)

| $C_{25}H_{33}H_5O_2$ (435.57) | | | | | | |
|---|---|---|---|---|---|---|
| Calc: | C | 68.94 | H | 7.64 | N | 16.08 |
| Found: | | 69.00 | | 7.66 | | 15.90 |

EXAMPLE 7

5,11-Dihydro-11-[[2-[3-(dimethylamino)propyl]-1-piperidinyl]carbonyl]-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[3-(dimethylamino)propyl]piperidine in a yield of 51% of theory. Colourless crystals, m.p. 142°–144° C. (from acetone and ethyl acetate), $R_f$ 0.7 (Macherey-Nagel, Polygram ® SIL G/UV$_{254}$, pre-coated plastic sheets for TLC; eluant: dichloromethane/cyclohexane/methanol/conc. ammonia 68/15/15/2, v/v/v/v)

| $C_{23}H_{29}N_5O_2$ (407.51) | | | | | | |
|---|---|---|---|---|---|---|
| Calculated: | C | 67.79 | H | 7.17 | N | 17.19 |
| Found: | | 67.80 | | 7.27 | | 16.99 |

EXAMPLE 8

5,11-Dihydro-11-[[4-[2-(1-piperidinyl)ethyl]-1-piperidinyl]carbonyl]-6H-pyrido[2,3-b][1,4]benzodiazepin-6-one

Prepared analogously to Example 4 from 11-(chlorocarbonyl)-5,11-dihydro-6H-pyrido[2,3-b][1,4]benzodiazepin-6-one and 4-[2-(1-piperidinyl)ethyl]piperidine in a yield of 47% of theory. Colourless crystals, m.p. 178°–180° C.

EXAMPLE 9

5,11-Dihydro-11-[[4-(1-methyl-4-piperidinyl)-1-piperidinyl]-carbonyl]-6H-pyrido[2,3-b][1,4]benzodiazepin-6-one-hydrochloride

Prepared analogously to Example 4 from 11-(chlorocarbonyl)-5,11-dihydro-6H-pyrido[2,3-b][1,4]benzodiazepin-6-one and 4-(1-methyl-4-piperidinyl)piperidine in a yield of 21% of theory. Colourless crystals, m.p. 254°–255° C.

EXAMPLE 10

5,11-Dihydro-11-[[2-[2-[[1-(phenylmethyl)-4-piperidinyl]-methylamino]ethyl]-1-pyrrolidinyl]carbonyl]-6H-pyrido[2,3-b][1,4]benzodiazepin-6-one

Prepared analogously to Example 1 from 11-(chlorocarbonyl)-5,11-dihydro-6H-pyrido[2,3-b][1,4]benzodiazepin-6-one and 2-[2-[[1-(phenylmethyl)-4-piperidinyl]methylamino]ethyl]pyrrolidine in a yield of 13% of theory. Amorphous resinous colourless substance, $R_f$ 0.06 (Merck DC ready made TLC plates, silica gel 60 $F_{254}$; eluant: dichloromethane/methanol/conc. ammonia 90/10/1, v/v/v)

| $C_{32}H_{38}N_6O_2$ (538.69) | | | | | | |
|---|---|---|---|---|---|---|
| Calc: | C | 71.35 | H | 7.11 | N | 15.60 |
| Found: | | 70.80 | | 7.34 | | 15.31 |

EXAMPLE 11

5,11-Dihydro-11-[[4-[3-(1-piperidinyl)propyl]-1-piperidinyl]carbonyl]-6H-pyrido[2,3-b][1,4]benzodiazepin-6-one

Prepared analogously to Example 4 from 11-(chlorocarbonyl)-5,11-dihydro-6H-pyrido[2,3-b][1,4]benzodiazepin-6-one and 4-[3-(1-piperidinyl)propyl]piperidine in a yield of 81% of theory. Colourless crystals, m.p. 200° C.

EXAMPLE 12

11-[[3-[3-(Diethylamino)propyl]-1-piperidinyl]carbonyl]-5,11-dihydro-6H-pyrido[2,3-b][1,4]benzodiazepin-6-one-hydrochloride

Prepared analogously to Example 1 from 11-(chlorocarbonyl)-5,11-dihydro-6H-pyrido[2,3-b][1,4]benzodiazepin-6-one and 3-[3-(diethylamino)propyl]piperidine in a yield of 84% of theory. Colourless crystals, m.p. 257°–258° C. (ethanol/diisopropylether)

| $C_{25}H_{34}ClN_5O_2$ (472.03) | | | | | | | | |
|---|---|---|---|---|---|---|---|---|
| Calc: | C | 63.61 | H | 7.26 | Cl | 7.51 | N | 14.84 |
| Found: | | 64.00 | | 7.35 | | 7.44 | | 14.88 |

EXAMPLE 13

5,11-Dihydro-11-[[3-[3-(dimethylamino)propyl]-1piperidinyl-]carbonyl]-6H-pyrido[2,3-b][1,4]benzodiazepin-6-one

Prepared analogously to Example 1 from 11-(chlorocarbonyl)-5,11-dihydro-6H-pyrido[2,3-b][1,4]benzodiazepin-6-one and 3-[3-(dimethylamino)propyl]piperidine in a yield of 71% of theory. Colourless crystals, m.p. 115°–117° C. (ethanol/ether 1:30, v/v), $R_f$ 0.35 (Merck DC ready made TLC plates, silica gel 60 $F_{254}$; eluant: dichloromethane/methanol/conc. ammonia 90/10/1, v/v/v)

The monohydrochloride melted at 222°–224° C.

| $C_{23}H_{30}ClN_5O_2$ (443.98) | | | | | | | | |
|---|---|---|---|---|---|---|---|---|
| Calc: | C | 62.22 | H | 6.81 | Cl | 7.99 | N | 15.77 |
| Found: | | 62.00 | | 7.07 | | 7.79 | | 15.58 |

EXAMPLE 14

5,11-Dihydro-11-[[3-[3-(4-morpholinyl)propyl]-1-piperidinyl]carbonyl]-6H-pyrido[2,3-b][1,4]benzodiazepin-6-one-hydrochloride

Prepared analogously to Example 1 from 11-(chlorocarbonyl)-5,11-dihydro-6H-pyrido[2,3-b][1,4]benzodiazepin-6-one and 3-[3-(4-morpholinyl)propyl]piperidine in a yield of 61% of theory. Colourless crystals, m.p. >260° C. (from ethanol/water/acetone).

| $C_{25}H_{32}ClN_5O_3$ (486.01) | | | | | | | | |
|---|---|---|---|---|---|---|---|---|
| Calc: | C | 61.78 | H | 6.64 | Cl | 7.29 | N | 14.41 |
| Found: | | 61.41 | | 6.68 | | 7.26 | | 14.18 |

EXAMPLE 15

5,11-Dihydro-11-[[3-3-(hexahydro-1H-1-azepinyl)-propyl]-1-piperidinyl]carbonyl]-6H-pyrido[2,3-b][1,4]benzodiazepin-6-one hydrochloride

Prepared analogously to Example 1 from 11-(chlorocarbonyl)-5,11-dihydro-6H-pyrido[2,3-b][1,4]benzodiazepin-6-one and 3-[3-(hexahydro-1H-1-azepinyl)propyl]piperidine in a yield of 60% of theory. Colourless crystals, m.p. >260° C., $R_f$ 0.4 (Merck, DC ready made TLC plates, silica gel 60 $F_{254}$; eluant: dichloromethane/methanol/conc. ammonia 90/10/1, v/v/v)

| $C_{27}H_{36}ClN_5O_2$ (498.07) | | | | | | | | |
|---|---|---|---|---|---|---|---|---|
| Calc: | C | 65.11 | H | 7.28 | Cl | 7.12 | N | 14.06 |
| Found: | | 65.51 | | 7.21 | | 7.18 | | 13.92 |

EXAMPLE 16

5,11-Dihydro-11-[[3-[3-(1-pyrrolidinyl)propyl]-1-piperidinyl]carbonyl]-6H-pyrido[2,3-b][1,4]benzodiazepin-6-one-hydrochloride

Prepared analogously to Example 1 from 11-(chlorocarbonyl)-5,11-dihydro-6H-pyrido[2,3-b][1,4]benzodiazepin-6-one and 3-[3-(1-pyrrolidinyl)propyl]piperidine in a yield of 56% of theory. Colourless crystals, m.p. >260° C. (from water/acetone), water solubility: about 0.3%.

| $C_{25}H_{32}ClN_5O_2$ (470.01) | | | | | | | |
|---|---|---|---|---|---|---|---|
| Calc: | C | 63.89 | H | 6.86 | Cl | 7.54 | N | 14.90 |
| Found: | | 63.90 | | 6.92 | | 7.25 | | 14.86 |

EXAMPLE 17

5,11-Dihydro-11-[[2-[4-(1-piperidinyl)butyl]-1-piperidinyl]carbonyl]-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[4-(1-piperidinyl)butyl]piperidine in a yield of 41% of theory. Colourless crystals, m.p. 199°–201° C. (after being recrystallised twice from ethanol using animal charcoal).

| $C_{27}H_{35}N_5O_2$ (461.61) | | | | | | |
|---|---|---|---|---|---|---|
| Calc: | C | 70.25 | H | 7.64 | N | 15.17 |
| Found: | | 70.07 | | 7.58 | | 15.02 |

EXAMPLE 18

5,11-Dihydro-11-[[3-[2-(dipropylamino)ethyl]-1-piperidinyl]carbonyl]-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[2-(dipropylamino)ethyl]piperidine in a yield of 67% of theory. Colourless crystals, m.p. 202°–205° C. (ethanol).

| $C_{26}H_{36}ClN_5O_2$ (486.06) | | | | | | | |
|---|---|---|---|---|---|---|---|
| Calc: | C | 64.25 | H | 7.46 | Cl | 7.29 | N | 14.41 |
| Found: | | 64.00 | | 7.39 | | 7.41 | | 14.25 |

EXAMPLE 19

5,11-Dihydro-11-[[3-[4-(dimethylamino)butyl]-1-piperidinyl]carbonyl]-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[4-(dimethylamino)butyl]piperidine in a yield of 69% of theory. Colourless crystals, m.p. 234°–235° C. (isopropanol).

| $C_{24}H_{32}ClN_5O_2$ (458.0) | | | | | | | |
|---|---|---|---|---|---|---|---|
| Calc: | C | 62.94 | H | 7.04 | Cl | 7.74 | N | 15.29 |
| Found: | | 63.03 | | 6.90 | | 7.90 | | 14.89 |

EXAMPLE 20

5,11-Dihydro-11-[[3-[4-(1-pyrrolidinyl)butyl]-1-piperidinyl]carbonyl]-6H-pyrido[2,3-b][1,4]benzodiazepin-6-one Prepared analogously to Example 1 from 11-(chlorocarbonyl)-5,11-dihydro-6H-pyrido[2,3-b][1,4]benzodiazepin-6-one and 3-[4-(1-pyrrolidinyl)butyl]piperidine in a yield of 50% of theory. Colourless crystals, m.p. 153°–156° C. (ethyl acetate/diethylether 1/1, v/v), $R_f$ 0.25 (Merck DC ready made TLC plates, silica gel 60 $F_{254}$; eluant: dichloromethane/methanol/conc. ammonia 90/10/1, v/v/v).

| $C_{26}H_{33}N_5O_2$ (447.58) | | | | | | |
|---|---|---|---|---|---|---|
| Calc: | C | 69.77 | H | 7.43 | N | 15.65 |
| Found: | | 69.72 | | 7.27 | | 15.25 |

EXAMPLE 21

6,11-Dihydro-11-[[3-[3-(1-piperidinyl)propyl]1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[3-(1-piperidinyl)propyl]piperidine in a yield of 58% of theory. Colourless crystals, m.p. 165.5°–167.0° C. (acetonitrile).

| $C_{26}H_{33}N_5O_2$ (447.58) | | | | | | |
|---|---|---|---|---|---|---|
| Calc: | C | 69.77 | H | 7.43 | N | 15.65 |
| Found: | | 69.65 | | 7.44 | | 15.50 |

EXAMPLE 22

11-[[3-[2-[(Cyclopentyl)methylamino]ethyl]-1-piperidinyl]carbonyl]-6,11-dihydro-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[2-[(cyclopentyl)methylamino]ethyl]piperidine in a yield of 61% of theory. Colourless crystals, m.p. 148°–150° C. (acetonitrile).

| $C_{26}H_{33}N_5O_2$ (447.58) | | | | | | |
|---|---|---|---|---|---|---|
| Calc: | C | 69.77 | H | 7.43 | N | 15.65 |
| Found: | | 69.75 | | 7.55 | | 15.76 |

EXAMPLE 23

5,11-Dihydro-11-[[3-[2-(1-piperidinyl)ethyl]-1-piperidinyl]carbonyl]-6H-pyrido[2,3-b][1,4]benzodiazepin-6-one-methanesulphonate Prepared analogously to Example 1 from 11-(chlorocarbonyl)-5,11-dihydro-6H-pyrido[2,3-b][1,4]benzodiazepin-6-one and 3-[2-(1-piperidinyl)ethyl]piperidine in a yield of 66% of theory. Colourless crystals, m.p. 231°–234° C. (ethanol).

| $C_{26}H_{35}N_5O_5S$ (529.65) | | | | | | | |
|---|---|---|---|---|---|---|---|
| Calc: | C | 58.96 | H | 6.66 | N | 13.22 | S | 6.05 |
| Found: | | 58.84 | | 6.69 | | 13.07 | | 6.26 |

EXAMPLE 24

11-[[3-[4-(Diethylamino)butyl]-1-piperidinyl]carbonyl]-5,11-dihydro-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[4-(diethylamino)- butyl]piperidine in a yield of 90% of theory. Colourless crystals, m.p. 182°–184° C. (ethanol).

| $C_{26}H_{36}ClN_5O_2$ (486.06) | | | | | | | | |
|---|---|---|---|---|---|---|---|---|
| Calc: | C | 64.25 | H | 7.46 | Cl | 7.29 | N | 14.41 |
| Found: | | 63.80 | | 7.62 | | 7.35 | | 13.49 |

EXAMPLE 25

9-Chloro-5,11-dihydro-11-[[3-[2-(1-pyrrolidinyl)ethyl]-1-piperidinyl]carbonyl]-6H-pyrido[2,3-b][1,4]benzodiazepin-6-one Prepared analogously to Example 1 from 9-chloro-11-(chlorocarbonyl)-5,11-dihydro-6H-pyrido[2,3-b][1,4]-benzodiazepin-6-one and 3-[2-(1-pyrrolidinyl)ethyl]piperidine in a yield of 42% of theory. Colourless crystals, m.p. 136°–139° C., $R_f$ 0.25 (Merck DC ready made TLC plates, silica gel 60 $F_{254}$; eluant: dichloromethane/methanol/conc. ammonia 90/10/1, v/v/v).

| $C_{24}H_{28}ClN_5O_2$ (453.97) | | | | | | | | |
|---|---|---|---|---|---|---|---|---|
| Calc: | C | 63.50 | H | 6.22 | Cl | 7.81 | N | 15.43 |
| Found: | | 63.41 | | 6.43 | | 7.70 | | 15.52 |

EXAMPLE 26

5,11-Dihydro-11-[[3-[2-(methylethylmethylamino)ethyl]-1-piperidinyl]carbonyl]-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[2-(methylethylmethylamino)ethyl]piperidine in a yield of 38% of theory. Colourless crystals, m.p. 196°–198° C. (D.), $R_f$ 0.21 (Merck DC ready made TLC plates, silica gel 60 $F_{254}$; eluant: dichloromethane/methanol/conc. ammonia 90/10/1, v/v/v).

| $C_{25}H_{34}ClN_5O_2$ (472.03) | | | | | | | | |
|---|---|---|---|---|---|---|---|---|
| Calc: | C | 63.61 | H | 7.26 | Cl | 7.51 | N | 14.84 |
| Found: | | 63.55 | | 7.37 | | 7.61 | | 14.61 |

EXAMPLE 27

11-[[4-[2-(Diethylamino)ethyl]-1-piperidinyl]carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 4-[2-(diethylamino)ethyl]piperidine in a yield of 34% of theory. Colourless crystals, m.p. 154° C. (ethyl acetate).

EXAMPLE 28

5,11-Dihydro-11-[[3-[2-(1-pyrrolidinyl)ethyl]-1-piperidinyl]carbonyl]-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[2-(1-pyrrolidinyl)ethyl]piperidine in a yield of 58% of theory. Colourless crystals, $R_f$ 0.25 (Merck DC ready made TLC plates, silica gel 60 $F_{254}$; eluant: dichloromethane/methanol/conc. ammonia 90/10/1, v/v/v).

| $C_{24}H_{30}ClN_5O_2$ (455.99) | | | | | | | | |
|---|---|---|---|---|---|---|---|---|
| Calc: | C | 63.22 | H | 6.63 | Cl | 7.78 | N | 15.36 |
| Found: | | 63.10 | | 6.76 | | 7.63 | | 15.21 |

EXAMPLE 29

11-[[3-[2-[(Cyclopentyl)methylamino]ethyl]-1-piperidinyl]carbonyl]-5,11-dihydro-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[2-[(cyclopentyl)methylamino]ethyl]piperidine in a yield of 54% of theory. Colourless crystals, m.p. 244°–246° C. (ethanol), $R_f$ 0.31 (Merck DC ready made TLC plates, silica gel 60 $F_{254}$; eluant: dichloromethane/methanol/conc. ammonia 90/10/1, v/v/v).

| $C_{26}H_{34}ClN_5O_2$ (484.04) | | | | | | | | |
|---|---|---|---|---|---|---|---|---|
| Calc: | C | 64.52 | H | 7.08 | Cl | 7.32 | N | 14.47 |
| Found: | | 64.33 | | 7.11 | | 7.53 | | 14.39 |

EXAMPLE 30

5,11-Dihydro-11-[[3-[2-(hexahydro-1H-1-azepinyl)ethyl]-1-piperidinyl]carbonyl]-6H-pyrido[2,3-b][1,4]benzodiazepin-6-one-hydrochloride Prepared analogously to Example 1 from 11-(chlorocarbonyl)-5,11-dihydro-6H-pyrido[2,3-b][1,4]benzodiazepin-6-one and 3-[2-(hexahydro-1H-1-azepinyl)ethyl]piperidine in a yield of 78% of theory. Colourless crystals, m.p. 255°–257° C. (ethanol/water/acetone 45/5/50, v/v/v), $R_f$ 0.27 (Merck DC ready made TLC plates, silica gel 60 $F_{254}$; eluant: dichloromethane/methanol/conc. ammonia 90/10/1, v/v/v).

| $C_{26}H_{34}ClN_5O_2$ (484.04) | | | | | | | | |
|---|---|---|---|---|---|---|---|---|
| Calc: | C | 64.52 | H | 7.08 | Cl | 7.32 | N | 14.47 |
| Found: | | 64.39 | | 7.17 | | 7.50 | | 14.29 |

EXAMPLE 31

5,11-Dihydro-11-[[3-[2-(methylethylamino)ethyl]-1-piperidinyl]carbonyl]-6H-pyrido[2,3-b][1,4]benzodiazepin-6-one hydrochloride Prepared analogously to Example 1 from 11-(chlorocarbonyl)-5,11-dihydro-6H-pyrido[2,3-b][1,4]benzodiazepin-6-one and 3-[2-(methylethylamino)ethyl]piperidine in a yield of 43% of theory. Colourless crystals, m.p. 228°–230° C., $R_f$ 0.39 (Merck DC ready made TLC plates, silica gel 60 $F_{254}$; eluant: dichloromethane/methanol/conc. ammonia 90/10/1, v/v/v).

| $C_{25}H_{34}ClN_5O_2$ (472.03) | | | | | | | | |
|---|---|---|---|---|---|---|---|---|
| Calc: | C | 63.61 | H | 7.26 | Cl | 7.51 | N | 14.84 |
| Found: | | 63.27 | | 7.40 | | 7.81 | | 14.80 |

EXAMPLE 32

6,11-Dihydro-11-[[3-[3-(1-pyrrolidinyl)propyl]-1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[3-(1-pyrrolidinyl)propyl]piperidine in a yield of 56% of theory. Colourless crystals, m.p. 174°–176° C. (acetonitrile), $R_f$ 0.65 (Macherey-Nagel, Polygram ® SIL G/UV$_{254}$, pre-coated plastic sheets for TLC; eluant: dichloromethane/cyclohexane/methanol/conc. ammonia 68/15/15/2, v/v/v/v)

| $C_{25}H_{31}N_5O_2$ (433.55) | | | | | | |
|---|---|---|---|---|---|---|
| Calc: | C | 69.26 | H | 7.21 | N | 16.15 |
| Found: | | 69.20 | | 7.19 | | 16.45 |

EXAMPLE 33

6,11-Dihydro-11-[[3-[2-(hexahydro-1H-1-azepinyl)ethyl]-1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[2-(hexahydro-1H-1-azepinyl)ethyl]piperidine in a yield of 58% of theory. Colourless crystals, m.p. 152°–154° C. (acetonitrile), $R_f$ 0.64 (Macherey-Nagel, Polygram ® SIL G/UV$_{254}$, pre-coated plastic sheets for TLC; eluant: dichloromethane/cyclohexane/methanol/conc. ammonia 68/15/15/2, v/v/v/v)

| $C_{26}H_{33}N_5O_2$ (447.58) | | | | | | |
|---|---|---|---|---|---|---|
| Calc: | C | 69.77 | H | 7.43 | N | 15.65 |
| Found: | | 69.74 | | 7.51 | | 15.64 |

EXAMPLE 34

6,11-Dihydro-11-[[4-[4-(1-pyrrolidinyl)butyl]-1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 4-[4-(1-pyrrolidinyl)butyl]piperidine in a yield of 72% of theory. Colourless crystals, m.p. 193°–195° C. (ethanol).

| $C_{26}H_{33}N_5O_2$ (447.58) | | | | | | |
|---|---|---|---|---|---|---|
| Calc: | C | 69.77 | H | 7.43 | N | 15.65 |
| Found: | | 69.97 | | 7.45 | | 15.78 |

EXAMPLE 35

4-[[3-[3-(Diethylamino)propyl]-1-piperidinyl]carbonyl]-4,9-dihydro-3-methyl-10H-thieno[3,4-b][1,5]benzodiazepin-10-one Prepared analogously to Example 4 from 4-(chlorocarbonyl)-4,9-dihydro-3-methyl-10H-thieno[3,4-b][1,5]benzodiazepin-10-one and 3-[3-(diethylamino)propyl]piperidine in a yield of 34% of theory. Colourless crystals, m.p. 136.0°–137.5° C. (diisopropylether).

EXAMPLE 36

4,9-Dihydro-4-[[3-[3-(dimethylamino)propyl]-1-piperidinyl]carbonyl]-3-methyl-10H-thieno[3,4-b][1,5]benzodiazepin-10-one Prepared analogously to Example 4 from 4-(chlorocarbonyl)-4,9-dihydro-3-methyl-10H-thieno[3,4-b][1,5]benzodiazepin-10-one and 3-[3-(dimethylamino)propyl]piperidine in a yield of 35% of theory. Colourless crystals, m.p. 137°–139° C. (acetonitrile).

| $C_{23}H_{30}N_4O_2S$ (426.58) | | | | | | | | |
|---|---|---|---|---|---|---|---|---|
| Calc: | C | 64.76 | H | 7.09 | N | 13.13 | S | 7.52 |
| Found: | | 64.77 | | 7.25 | | 13.07 | | 7.75 |

EXAMPLE 37

6,11-Dihydro-11-[[-3-[3-(1-piperidinyl)propyl]-1-piperidinyl]carbonyl]-5H-pyrido[2,3-b][1,5]benzodiazepin-5-one To a mixture consisting of 22.5 ml of a 20% solution of phosgene in toluene, 100 ml of acetonitrile and 4.75 g (0.045 mol) of anhydrous sodium carbonate, 8.94 g (0.0425 mol) of 3-[3-(1-piperidinyl)propyl]piperidine were added dropwise with external cooling with ice. The mixture was stirred for a further 60 minutes at ambient temperature, then 9.0 g (0.0428 mol) of 6,11-dihydro-5H-pyrido[2,3-b][1,5]benzodiazepin-5-one were added to the reaction mixture and this was then refluxed for 4 hours. The boiling hot mixture was filtered, the precipitate was thoroughly washed with three times 10 ml of hot acetonitrile and the combined filtrates were evaporated down in vacuo to a total volume of 50 ml. This was left to cool and kept at 0° to 5° C. for 2 hours with occasional stirring using a glass rod, the crystal slurry obtained was suction filtered, recrystallised from acetonitrile and colourless crystals were obtained, m.p. 166°–167° C., which were identical according to their mixed melting point, IR and $^1$H-NMR spectrum, to a preparation prepared according to Example 21.

Yield: 6.2 g (33% of theory).

The following were obtained correspondingly:

5,11-dihydro-11-[[3-[3-(1-piperidinyl)propyl]1-piperidinyl]carbonyl]-6H-pyrido[2,3-b][1,4]benzodiazepin-6-one, m.p. 123.5°–125.5° C. (acetonitrile);

11-[[3-[3-(diethylamino)propyl]-1-piperidinyl]carbonyl]-5,11-dihydro-6H-pyrido[2,3-b][1,4]benzodiazepin-6-one, which, after being converted into the monohydrochloride, melted at 257.5°–259.0° C. (ethanol);

11-[[3-[2-[(cyclopentyl)methylamino]ethyl]-1-piperidinyl]carbonyl]-6,11-dihydro-5H-pyrido[2,3-b][1,5]benzodiazepin-5-one, m.p. 149°–150° C. (acetonitrile);

5,11-dihydro-11-[[3-[2-(1-piperidinyl)ethyl]-1-piperidinyl]carbonyl]-6H-pyrido[2,3-b][1,4]benzodiazepin-6-one, which when converted into the methanesulphonate melted at 233°–234° C. (ethanol).

EXAMPLE 38

5,11-Dihydro-11-[[3-[2-(1-piperidinyl)ethyl]-1-pyrrolidinyl]carbonyl]-6H-pyrido2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 3-[2-(1-piperidinyl)ethyl]pyrrolidine in a yield of 75% of theory. Colourless crystals, m.p. 234°–236° C. (methanol).

| $C_{24}H_{29}N_5O_2$ (419.53) | | | | | | |
|---|---|---|---|---|---|---|
| Calc: | C | 68.71 | H | 6.97 | N | 16.69 |
| Found: | | 68.38 | | 7.05 | | 16.70 |

EXAMPLE 39

6,11-Dihydro-11-[[3-[3-(4-morpholinyl)propyl]-1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[3-(4-morpholinyl)propyl]piperidine in a yield of 43% of theory. Colourless crystals, m.p. 161°–163° C. (acetonitrile).

| $C_{25}H_{31}N_5O_3$ (449.55) | | | | | | |
|---|---|---|---|---|---|---|
| Calc: | C | 66.79 | H | 6.95 | N | 15.58 |
| Found: | | 66.21 | | 6.99 | | 15.63 |

The monohydrochloride melted at 221°–223° C.

EXAMPLE 40

6,11-Dihydro-11-[[3-[2-(1-piperidinyl)ethyl]-1-piperidinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[2-(1-piperidinyl)ethyl]piperidine in a yield of 50% of theory. Colourless crystals, m.p. 168°–169° C. (acetonitrile).

| $C_{25}H_{31}N_5O_2$ (433.55) | | | | | | |
|---|---|---|---|---|---|---|
| Calc: | C | 69.26 | H | 7.21 | N | 16.15 |
| Found: | | 69.22 | | 7.20 | | 16.04 |

EXAMPLE 41

11-[[3-[2-(Diethylamino)ethyl]-1-piperidinyl]carbonyl]-6,11-dihydro-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[2-(diethylamino)ethyl]piperidine in a yield of 54% of theory. Colourless crystals, m.p. 110°–113° C. (acetonitrile).

| $C_{24}H_{31}N_5O_2$ (421.54) | | | | | | |
|---|---|---|---|---|---|---|
| Calc: | C | 68.38 | H | 7.41 | N | 16.61 |
| Found: | | 69.00 | | 7.73 | | 16.56 |

EXAMPLE 42

11-[[3-[3-(Diethylamino)propyl]-1-piperidinyl]carbonyl]-6,11-dihydro-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 3-[3-(diethylamino)propyl]piperidine in a yield of 38% of theory. Colourless crystals, m.p. 123°–125° C. (acetonitrile).

| $C_{25}H_{33}N_5O_2$ (435.57) | | | | | | |
|---|---|---|---|---|---|---|
| Calc: | C | 68.94 | H | 7.64 | N | 16.08 |
| Found: | | 68.80 | | 7.64 | | 15.79 |

EXAMPLE 43

11-[[4-[4-(Diethylamino)butyl]-1-piperidinyl]carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 4-[4-(diethylamino)butyl]piperidine in a yield of 62% of theory. Colourless crystals, m.p. 126°–127° C.

| $C_{26}H_{35}N_5O_2$ (449.59) | | | | | | |
|---|---|---|---|---|---|---|
| Calc: | C | 69.46 | H | 7.85 | N | 15.58 |
| Found: | | 69.18 | | 7.86 | | 15.70 |

EXAMPLE 44

9-Chloro-11-[[4-[4-(diethylamino)butyl]-1-piperidinyl]carbonyl]-5,11-dihydro-6H-pyrido[2,3-b][1,4]benzodiazepin-6-one Prepared analogously to Example 4 from 9-chloro-11-(chlorocarbonyl)-5,11-dihydro-6H-pyrido[2,3-b][1,4]-benzodiazepin-6-one and 4-[4-(diethylamino)butyl]piperidine in a yield of 38% of theory. Colourless crystals, m.p. 126°–127° C.

| $C_{26}H_{34}ClN_5O_2$ (484.04) | | | | | | | | |
|---|---|---|---|---|---|---|---|---|
| Calc: | C | 64.52 | H | 7.08 | N | 14.47 | Cl | 7.32 |
| Found: | | 64.12 | | 7.23 | | 14.53 | | 7.37 |

EXAMPLE 45

3-Methyl-4-[[4-[4-(1-piperidinyl)butyl]-1-piperidinyl]carbonyl]-4,9-dihydro-10H-thieno[3,4-b][1,5]benzodiazepin-10-one Prepared analogously to Example 4 from 4-(chlorocarbonyl)-4,9-dihydro-3-methyl-10H-thieno[3,4-b][1,5]benzodiazepin-10-one and 4-[4-(1-piperidinyl)butyl]piperidine in a yield of 31% of theory. Colourless crystals, m.p. 209°–210° C. (ethyl acetate).

EXAMPLE 46

11-[[2-[2-[[3-(Diethylamino)propyl]methylamino]ethyl]-1-piperidinyl]carbonyl]-5,11-dihydro-6H-pyrido[2,3-b]1,4]-benzodiazepin-6-one Prepared analogously to Example 4 from 11-(chlorocarbonyl)-5,11-dihydro-6H-pyrido[2,3-b][1,4]benzodiazepin-10-one and 2-[2-[[3-(diethylamino)propyl]methylamino]ethyl]piperidine (b.p.$_{0.1}$ $mmHg$ 130°–134° C.) in a yield of 80% of theory. Colourless crystals, m.p. 123°–125° C. (acetonitrile).

| $C_{28}H_{40}N_6O_2$ (492.66) | | | | | | |
|---|---|---|---|---|---|---|
| Calc: | C | 68.26 | H | 8.18 | N | 17.06 |
| Found: | | 68.08 | | 8.30 | | 17.34 |

EXAMPLE 47

11-[[2-[2-[2-(Diethylamino)ethoxy]ethyl]-1-piperidinyl]carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[2-[2-(diethylamino)ethoxy]ethyl]piperidine (b.p.$_{0.4}$ $mmHg$ 95°–99° C.) in a yield of 79% of theory. Colourless crystals, m.p. 134°–136° C. (acetonitrile).

| $C_{26}H_{35}N_5O_3$ (465.59) | | | | | | |
|---|---|---|---|---|---|---|
| Calc: | C | 67.07 | H | 7.58 | N | 15.04 |
| Found: | | 67.14 | | 7.64 | | 15.16 |

EXAMPLE 48

4-[[2-[2-[[2-(Diethylamino)ethyl]methylamino]ethyl]-1-piperidinyl]carbonyl]-4,9-dihydro-3-methyl-10H-thieno[3,4-b][1,5]benzodiazepin-10-one Prepared analogously to Example 4, but using dichloromethane instead of acetonitrile as solvent, from 4-(chlorocarbonyl)-4,9-dihydro-3-methyl-10H-thieno[3,4-b][1,5]benzodiazepin-10-one and 2-[2-[[2-(diethylamino)ethyl]methylamino]ethyl]piperidine (b.p.$_{0.3}$ $mmHg$ 92°–95° C.) in a yield of 22% of theory. Colourless crystals, m.p. 131°–133° C. (acetonitrile).

| $C_{27}H_{39}N_5O_2S$ (497.70) | | | | | | | | |
|---|---|---|---|---|---|---|---|---|
| Calc. | C | 65.16 | H | 7.90 | N | 14.07 | S | 6.44 |
| Found: | | 65.00 | | 7.70 | | 14.00 | | 6.63 |

EXAMPLE 49

4-[[2-[2-[2-(Diethylamino)ethoxy]ethyl]-1-piperidinyl]-carbonyl]-4,9-dihydro-3-methyl-10H-thieno[3,4-b][1,5]-benzodiazepin-10-one Prepared analogously to Example 4 from 4-(chlorocarbonyl)-3-methyl-10H-thieno[3,4-b][1,5]benzodiazepin-10-one and 2-[2-[2-(diethylamino)ethoxy]ethyl]piperidine in a yield of 53% of theory. Colourless crystals, m.p. 105°–107° C. (diisopropylether).

| $C_{26}H_{36}N_4O_3S$ (484.66) | | | | | | | | |
|---|---|---|---|---|---|---|---|---|
| Calc: | C | 64.43 | H | 7.49 | N | 11.56 | S | 6.62 |
| Found: | | 64.00 | | 7.44 | | 11.70 | | 6.60 |

EXAMPLE 50

11-[[2-[2-[[3-(Diethylamino)propyl]methylamino]ethyl]-1-piperidinyl]carbonyl]-6,11-dihydro-5H-pyrido[2,3-b][1,5]benzodiazepin-5-one dihydrochloride hydrate Prepared analogously to Example 4 from 11-(chlorocarbonyl)-6,11-dihydro-5H-pyrido[2,3-b][1,5]benzodiazepin-5-one and 2-[2-[[3-(diethylamino)propyl]methylamino]ethyl]piperidine in a yield of 48% of theory. The colourless dihydrochloride-hydrate melted at 145°–150° C. (D.).

| $C_{28}H_{40}N_6O_2 \times 2HCl \times H_2O$ (583.60) | | | | | | | | |
|---|---|---|---|---|---|---|---|---|
| Calc: | C | 57.63 | H | 7.60 | Cl | 12.15 | N | 14.40 |
| Found: | | 57.64 | | 7.80 | | 12.05 | | 14.49 |

EXAMPLE 51

11-[[3-[2-(Diethylamino)ethyl]-1-pyrrolidinyl]carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 3-[2-(diethylamino)ethyl]pyrrolidine in a yield of 13% of theory. Colourless crystals, m.p. 137°–138° C. (from ethyl acetate/methanol 98/2 v/v).

| $C_{23}H_{29}N_5O_2$ (407.51) | | | | | | |
|---|---|---|---|---|---|---|
| Calc: | C | 67.79 | H | 7.17 | N | 17.19 |
| Found: | | 67.19 | | 7.05 | | 17.15 |

EXAMPLE 52

5,11-Dihydro-11-[[4-[3-(4-methyl-1-piperazinyl)-propyl]-1-piperidinyl]carbonyl]-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 4-[3-(4-methyl-1-piperazinyl)propyl]piperidine in a yield of 17% of theory. Colourless crystals, m.p. 213°–214° C.; $R_f$ 0.25 (Merck DC ready-made TLC plates, silica gel 60 $F_{254}$; eluant: ethyl acetate/methanol/cyclohexane/conc. ammonia 80/10/10/1 v/v/v/v).

EXAMPLE 53

4-[[4-[2-[2-(Diethylamino)ethoxy]ethyl]-1-piperidinyl]-carbonyl]-4,9-dihydro-3-methyl-10H-thieno[3,4-b][1,5-benzodiazepin-10-one Prepared analogously to Example 4 from 4-(chlorocarbonyl)-4,9-dihydro-3-methyl-10H-thieno[3,4-b][1,5]benzodiazepin-10-one and 4-[2-[2-(diethylamino)ethoxy]ethyl]piperidine (b.p.$_{0.009}$ $mmHg$ 101°–102° C.) in a yield of 71% of theory. Colourless crystals, m.p. 125°–126° C (diisopropylether).

| $C_{26}H_{36}N_4O_3S$ (484.66) | | | | | | | | |
|---|---|---|---|---|---|---|---|---|
| Calc: | C | 64.43 | H | 7.49 | N | 11.56 | S | 6.62 |
| Found: | | 64.50 | | 7.27 | | 11.80 | | 6.52 |

EXAMPLE 54

11-[[4-[2-[2-(Diethylamino)ethoxy]ethyl]-1-piperidinyl]carbonyl]-5,11-dihydro-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 4-[2-[2-(diethylamino)e- thoxy]ethyl]piperidine in a yield of 71% of theory. Colourless crystals, m.p. 119°–120° C. (cyclohexane), $R_f$ 0.43 (Macherey-Nagel, Polygram ® SIL G/UV$_{254}$, pre-coated plastic sheets for TLC; eluant: ethyl acetate/methanol/conc. ammonia 100/30/3, v/v/v)

EXAMPLE 55

9-Chloro-11-[[4-[2-[2-(diethylamino)ethoxy]ethyl]-1-piperidinyl]carbonyl]-5,11-dihydro-6H-pyrido[2,3-b][1,4]benzodiazepin-6-one Prepared analogously to Example 4 from 9-chloro-11-(chlorocarbonyl)-5,11-dihydro-6H-pyrido[2,3-b][1,4]benzodiazepin-6-one and 4-[2-[2-(diethylamino)ethoxy]ethyl]piperidine in a yield of 43% of theory. Colourless crystals, m.p. 145°–146° C. (acetonitrile), $R_f$ 0.39 (conditions as in Example 54).

| $C_{26}H_{34}ClN_5O_3$ (500.04) | | | | | | | |
|---|---|---|---|---|---|---|---|
| Calc: | C | 62.45 | H | 6.85 | Cl | 7.09 | N | 14.01 |
| Found: | | 62.16 | | 6.97 | | 7.30 | | 14.12 |

EXAMPLE 56

11-[[4-[2-[2-(Diethylamino)ethoxy]ethyl]-1-piperidinyl]carbonyl]-6,11-dihydro-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 4-[2-[2-(diethylamino)ethoxy]ethyl]piperidine in a yield of 83% of theory. The colourless hydrochloride melted at 148°–150° C. (ethyl acetate).

| $C_{26}H_{36}ClN_5O_3$ (502.05) | | | | | | | |
|---|---|---|---|---|---|---|---|
| Calc: | C | 62.20 | H | 7.23 | Cl | 7.06 | N | 13.95 |
| Found: | | 61.96 | | 7.37 | | 7.20 | | 13.77 |

EXAMPLE 57

5,11-Dihydro-11-[[2-[2-(1-piperidinyl)ethyl]-4-morpholinyl]carbonyl]-6H-pyrido[2,3-b][1,4]benzodiazepin-6-one Prepared analogously to Example 4 from 11-(chlorocarbonyl)-5,11-dihydro-6H-pyrido[2,3-b][1,4]benzodiazepin-6-one and 2-[2-(1-piperidinyl)ethyl]morpholine ($R_f$ 0.4 [Macherey-Nagel, Polygram ® SIL G/UV$_{254}$, pre-coated plastic sheets for TLC; eluant: dichloromethane/methanol/cyclohexane/conc. ammonia 68/15/15/2, v/v/v/v]) in a yield of 79% of theory. The colourless hydrochloride melted at 274°–275° C.

| $C_{24}H_{30}ClN_5O_3$ (471.99) | | | | | | | |
|---|---|---|---|---|---|---|---|
| Calc: | C | 61.07 | H | 6.41 | Cl | 7.51 | N | 14.81 |
| Found: | | 60.86 | | 6.37 | | 7.69 | | 15.08 |

EXAMPLE 58

6,11-Dihydro-11-[[2-[2-(1-piperidinyl)ethyl]-4-morpholinyl]carbonyl]-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 2-[2-(1-piperidinyl)ethyl]morpholine in a yield of 78% of theory. Colourless crystals, m.p. 136°–138° C. (diisopropylether), $R_f$ 0.46 (Macherey-Nagel, Polygram ® SIL G/UV$_{254}$, pre-coated plastic sheets for TLC; eluant: ethyl acetate/methanol/conc. ammonia 100/30/3, v/v/v).

| $C_{24}H_{29}N_5O_3$ (435.52) | | | | | | |
|---|---|---|---|---|---|---|
| Calc: | C | 66.19 | H | 6.71 | N | 16.08 |
| Found: | | 66.01 | | 6.64 | | 16.10 |

EXAMPLE 59

5,11-Dihydro-8-methyl-11-[[2-[2-(1-piperidinyl)ethyl]-4-morpholinyl]carbonyl]-6H-pyrido[2,3-b][1,4]benzodiazepin-6-one Prepared analogously to Example 4 from 11-(chlorocarbonyl)-5,11-dihydro-8-methyl-6H-pyrido[2,3-b][1,4]benzodiazepin-6-one and 2-[2-(1-piperidinyl)ethyl]morpholine in a yield of 79% of theory. $R_f$ 0.43 (conditions as in Example 58). The colourless hydrochloride melted at 272°–273° C. with decomposition.

| $C_{25}H_{32}ClN_5O_3$ (486.01) | | | | | | | |
|---|---|---|---|---|---|---|---|
| Calc: | C | 61.78 | H | 6.64 | Cl | 7.29 | N | 14.41 |
| Found: | | 61.49 | | 6.65 | | 7.43 | | 14.50 |

EXAMPLE 60

11-[[2-[2-[2-(Diethylamino)ethoxy]ethyl]-1-piperidinyl]carbonyl]-6,11-dihydro-5H-pyrido[2,3-b][1,5]benzodiazepin-5-one Prepared analogously to Example 4 from 11-(chlorocarbonyl)-6,11-dihydro-5H-pyrido[2,3-b][1,5]benzodiazepin-5-one and 2-[2-[2-(diethylamino)ethoxy]ethyl]piperidine in a yield of 86% of theory. The colourless hydrochloride melted at 186°–187° C.

| $C_{26}H_{36}ClN_5O_3$ (502.05) | | | | | | | |
|---|---|---|---|---|---|---|---|
| Calc: | C | 62.20 | H | 7.23 | Cl | 7.06 | N | 13.95 |
| Found: | | 61.91 | | 7.13 | | 7.09 | | 13.90 |

EXAMPLE 61

4,9-Dihydro-3-methyl-4-[[2-[2-(1-piperidinyl)ethyl]-4-morpholinyl]carbonyl]-10H-thieno[3,4-b][1,5]benzodiazepin-10-one Prepared analogously to Example 4 from 4-(chlorocarbonyl)-4,9-dihydro-3-methyl-10H-thieno[3,4-b][1,5]benzodiazepin-10-one and 2-[2-(1-piperidinyl)ethyl]morpholine in a yield of 74% of theory. $R_f$ 0.48 (conditions as in Example 58). The colourless hydrochloride melted at 254°–256° C. (D.).

| $C_{24}H_{31}ClN_4O_3S$ (491.05) | | | | | | | | | |
|---|---|---|---|---|---|---|---|---|---|
| Calc: | C | 58.70 | H | 6.36 | Cl | 7.22 | N | 11.41 | S | 6.53 |
| Found: | | 58.51 | | 6.38 | | 7.31 | | 11.56 | | 6.71 |

The following Examples illustrate the preparation of some pharmaceutical forms:

EXAMPLE I

Tablets containing 5 mg of
5,11-dihydro-11-[[3-[3-(1-piperidinyl)propyl]-1-piperidinyl]carbonyl]-6H-pyrido[2,3-b][1,4]benzodiazepin-6-one

| Composition: 1 tablet contains: | |
|---|---|
| Active substance | 5.0 mg |
| Lactose | 148.0 mg |
| Potato starch | 65.0 mg |
| Magnesium stearate | 2.0 mg |
| | 220.0 mg |

Method of preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.

Weight of tablet: 220 mg
Punch: 9 mm

Example II

Coated tablets containing 5 mg of
5,11-dihydro-11-[[3-[3-(1-piperidinyl)propyl]-1-piperidinyl]carbonyl]-6H-pyrido[2,3-b][1,4]benzodiazepin-6-one The tablets prepared according to Example I are coated, by a known method, with a coating consisting essentially of sugar and talc. The finished coated tablets are polished with beeswax.

Weight of coated tablet: 300 mg

Example III

Ampoules containing 10 mg of
5,11-dihydro-11-[[3-[3-(1-piperidinyl)propyl]-1-piperidinyl]carbonyl]-6H-pyrido[2,3-b][1,4]benzodiazepin-6-one-methanesulphonate

| Composition: 1 ampoule contains: | |
|---|---|
| Acitve substance | 10.0 mg |
| Sodium chloride | 8.0 mg |
| Distilled water ad | 1 ml |

Method of preparation

The active substance and sodium chloride are dissolved in distilled water and then made up to the volume specified. The solution is sterile filtered and transferred into 1 ml ampoules.

Sterilisation: 20 minutes at 120° C.

Example IV

Suppositories containing 20 mg of
5,11-dihydro-11-[[3-[3-(1-piperidinyl)propyl]-1-piperidinyl]carbonyl]-6H-pyrido[2,3-b][1,4]benzodiazepin-6-one

| Composition 1 suppository contains: | |
|---|---|
| Active substance | 20.0 mg |
| Suppository mass (e.g. Witepsol W 45 ®) | 1 680.0 mg |
| | 1 700.0 mg |

Method of preparation

The finely powdered active substance is suspended in the molten suppository mass which has been cooled to 40° C. The mass is poured at 37° C. into slightly chilled suppository moulds.

Weight of suppository 1.7 g

Example V

Drops containing
5,11-dihydro-11-[[3-[3-(1-piperidinyl)propyl]-1-piperidinyl]carbonyl]-6H-pyrido[2,3-b][1,4]benzodiazepin-6-one-methanesulphonate

| Composition 100 ml of drops solution contain: | |
|---|---|
| Methyl p-hydroxybenzoate | 0.035 g |
| Propyl p-hydroxybenzoate | 0.015 g |
| Anisole | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water ad | 100.0 ml |

Method of preparation

The active substance and sodium cyclamate are dissolved in about 70 ml of water and glycerol is added. The p-hydroxybenzoates, anisole and menthol are dissolved in ethanol and this solution is added with stirring to the aqueous solution. Finally, the solution is made up to 100 ml with water and filtered to remove any suspended particles.

What is claimed is:

1. A condensed diazepinone of the formula (I)

wherein B is one of the divalent groups

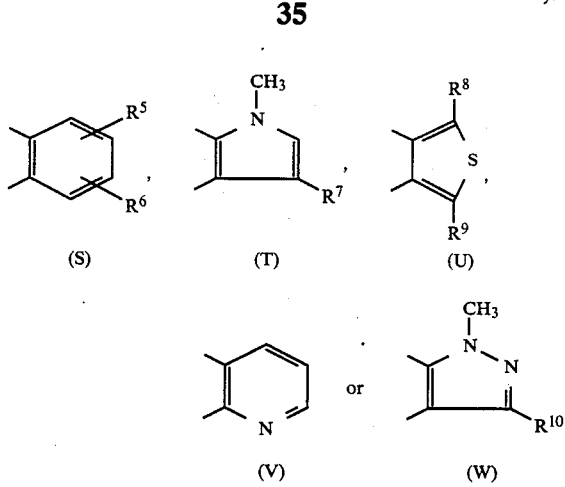

(S)  (T)  (U)

(V)  or  (W)

$X^1$ and $X^2$ are each a =CH— group or, if B is one of the above-mentioned diivalent groups (S), (U) or (W), both $X^1$ and $X^2$ or only $X^1$ or only $X^2$ may be a nitrogen atom;

A is a straight-chained or branched saturated alkylene group with two to seven carbon atoms which may also be interrupted by an oxygen of sulphur atom or by a methylimino or ethylimino group;

Z is a single bond, an oxygen or sulphur atom or a methylene or 1,2-ethylene group;

$R^1$ is a branched or unbranched alkyl group with 1 to 4 carbon atoms or a benzyl group;

$R^2$ is a branched or unbranched alkyl group with 1 to 7 carbon atoms which may optionally also be substituted by a hydroxy group at its 2nd to 7th carbon atom, a cycloalkyl or cycloalkylmethyl group with 3 to 7 carbon atoms in the ring, wherein the cycloalkyl ring may optionally also be substituted by a hydroxy group;

$R^1$ and $R^2$ may, however, also form, together with the intermediate nitrogen atom, a 1-piperidinyl, 4-morpholinyl, 2- or 3-hexahydro-1H-1-azepinyl, 1-pyrrolidinyl or 4-methyl-1-piperazinyl group;

$R^2$ may, however, also be linked to A via an alkylene bridge so that, in conjunction with the group $NR^1$, a saturated 5-, 6- or 7-membered heterocyclic ring system is produced;

$R^3$ is an alkyl group with 1 to 4 carbon atoms, a chlorine atom or a hydrogen atom;

$R^4$ is a hydrogen atom or a methyl group;

$R^5$ and $R^6$ are each a hydrogen atom, a fluorine, chlorine or bromine atom or an alkyl group with 1 to 4 carbon atoms;

$R^7$ is a hydrogen or chlorine atom or a methyl group;

$R^8$ is a hydrogen atom or an alkyl group with 1 to 4 carbon atoms;

$R^9$ is a hydrogen or halogen atom or an alkyl group with 1 to 4 carbon atoms and $R^{10}$ is a hydrogen atom or a methyl group, with the proviso that if B is the divalent group (T) and $R^7$ is a hydrogen atom, $R^3$ can not be a chlorine atom and Z can not be a sulphur atom, or a pharmaceutically acceptable salt thereof.

2. A condensed diazepinone of the Formula I, as claimed in claim 1, further characterized in that, either $X^1$ is a =CH— group, $X^2$ is a nitrogen atom and B is a divalent group (S), with the proviso that $R^3$, $R^4$ and $R^5$ are hydrogen atoms and $R^6$ is a hydrogen atom or a chlorine or bromine atom or a methyl or ethyl group in the 8 or 9 of the hetero- cycle, or, $X^1$ and $X^2$ are =CH— groups and B is the divalent group (U), wherein $R^8$ is a hydrogen atom and $R^9$ is a methyl group, or the group (V), wherein at least one of the groups $R^3$ and $R^4$ is a hydrogen atom, A is a two- to four- membered alkylene chain in the 3 or 4 position of the saturated heterocyclic ring, Z is a methylene group and $R^1$ and $R^2$ are each alkyl groups with 1 to 4 carbon atoms or together with the intermediate nitrogen atom form a 1-pyrrolidinyl, 1-piperidinyl, 4-morpholinyl or hexahydro-1H-1azepinyl group, or a pharmaceutically acceptable salt thereof.

3. 6,11-dihydro-11-[[3-[2-(1-piperidinyl)ethyl]- 1-piperidinyl]carbonyl]-5H-pyrido[2,3-b][1,5]benzodiazepin-5-one, or a pharmaceutically acceptable salt thereof.

4. 5,11-dihydro-11-[-[3-[3-[3-(1-piperidinyl)propyl]-1-piperidinyl]carbonyl]-6H-pyrido[2,3-b][1,4]benzodiazepin-6-one, or a pharmaceutically acceptable salt thereof.

5. A pharmaceutical composition suitable for the treatment of bradycardia or bradyarrhythmia comprising an amount of one or more compounds as claimed in claim 1,2,3 or 4 which is sufficient to treat bradycardia or bradyarryhthmia, together with conventional carriers and/or excipents.

6. A method for the treatment of bradycardia or bradyarrhythmia which comprises administering a pharmaceuticallly effective amount of a compound of formula I, as claimed in claim 1,2,3 or 4.

* * * * *